United States Patent [19]
Okada

[11] Patent Number: 5,871,440
[45] Date of Patent: Feb. 16, 1999

[54] ENDOSCOPE

[75] Inventor: Yuta Okada, Kokubunji, Japan

[73] Assignee: Olympus Optical Co., Ltd., Tokyo, Japan

[21] Appl. No.: 756,037

[22] Filed: Nov. 26, 1996

[30] Foreign Application Priority Data

| Dec. 15, 1995 | [JP] | Japan | 7-327498 |
| Dec. 19, 1995 | [JP] | Japan | 7-330563 |
| Jul. 19, 1996 | [JP] | Japan | 8-190745 |
| Jul. 30, 1996 | [JP] | Japan | 8-200354 |

[51] Int. Cl.$^6$ ........................................ A61B 1/06
[52] U.S. Cl. ........................ 600/129; 600/176; 600/158
[58] Field of Search ............................. 600/101, 129, 600/153, 156, 157, 158, 160, 173, 176, 177

[56] References Cited

U.S. PATENT DOCUMENTS

| 3,901,220 | 8/1975 | Koyasu | 600/176 |
| 4,319,563 | 3/1982 | Kubota | 600/129 |
| 4,580,552 | 4/1986 | Nishioka | 600/177 |
| 4,807,597 | 2/1989 | Tsuno et al. | |
| 4,838,247 | 6/1989 | Forkner | 600/171 |
| 4,841,952 | 6/1989 | Sato | 600/129 |
| 4,879,991 | 11/1989 | Ogiu | 600/129 |
| 5,184,602 | 2/1993 | Anapliotis | 600/176 |
| 5,305,736 | 4/1994 | Ito | 600/176 |
| 5,509,892 | 4/1996 | Bonnet | 600/129 |
| 5,554,100 | 9/1996 | Leiner | 600/129 |
| 5,695,447 | 12/1997 | Yabe | 600/129 |
| 5,700,236 | 7/1996 | Sauer | 600/129 |
| 5,718,664 | 6/1995 | Peck | 600/160 |

FOREIGN PATENT DOCUMENTS

| 64-9854 | 2/1989 | Japan . |
| 64-36816 | 3/1989 | Japan . |
| 4-102432 | 4/1992 | Japan . |
| 4-50002 | 4/1992 | Japan . |
| 5-5530 | 2/1993 | Japan . |
| 5-37649 | 6/1993 | Japan . |
| 7-43621 | 2/1995 | Japan . |
| 7-116109 | 5/1995 | Japan . |

*Primary Examiner*—Gene Mancene
*Assistant Examiner*—Ira Hatton
*Attorney, Agent, or Firm*—Fishauf, Holtz, Goodman, Langer & Chick

[57] ABSTRACT

An endoscope having an insertion section to be inserted into a tubular cavity, an observation lens provided in a distal end of the insertion section, and a rounded distal portion protruding from the distal end of the insertion section in the insertion direction. The observation lens is positioned with its center displaced from the forwardmost tip of the rounded distal portion.

23 Claims, 18 Drawing Sheets

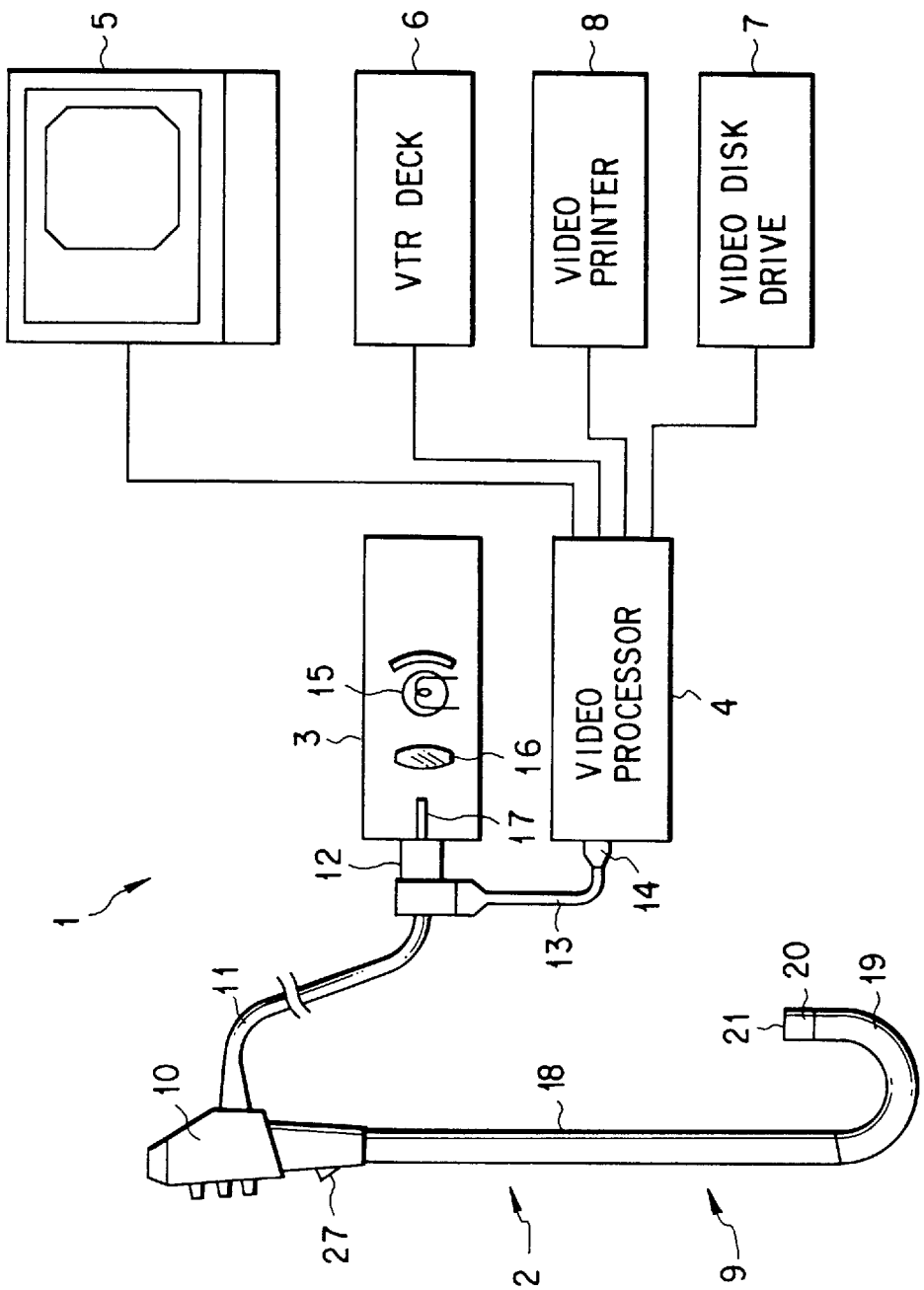
F I G. 1

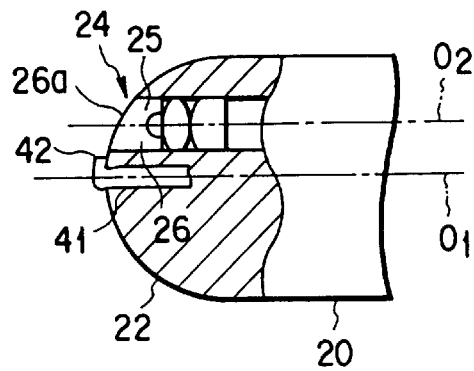
F I G. 4
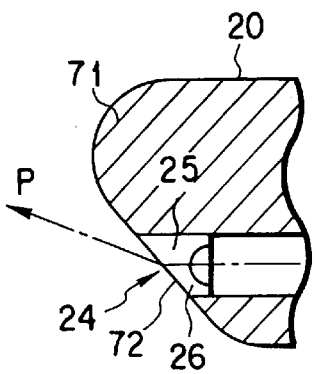
F I G. 5
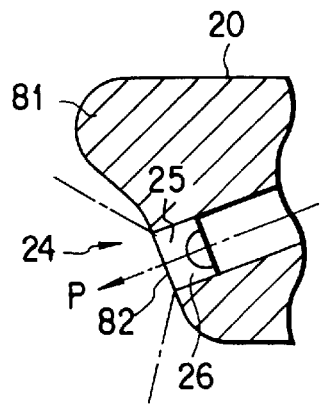
F I G. 6A
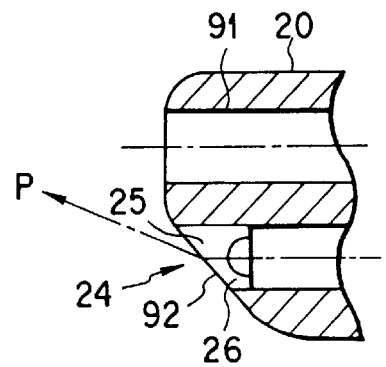
F I G. 6B

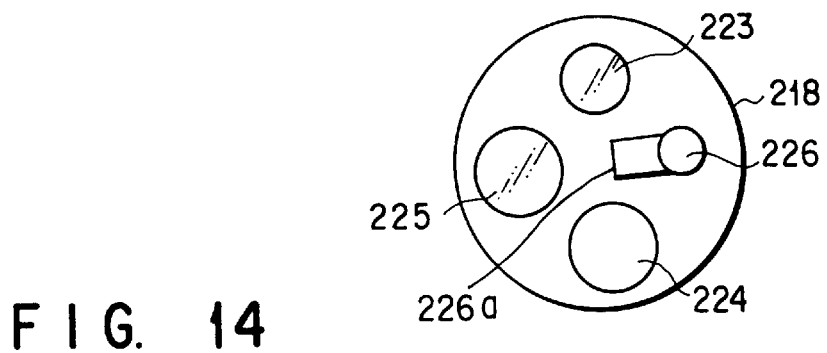
F I G. 14
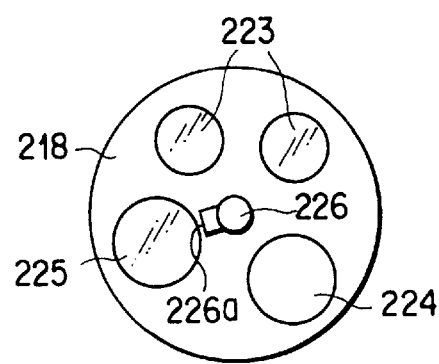
F I G. 15
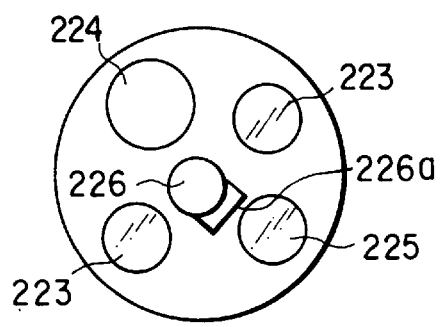
F I G. 16A
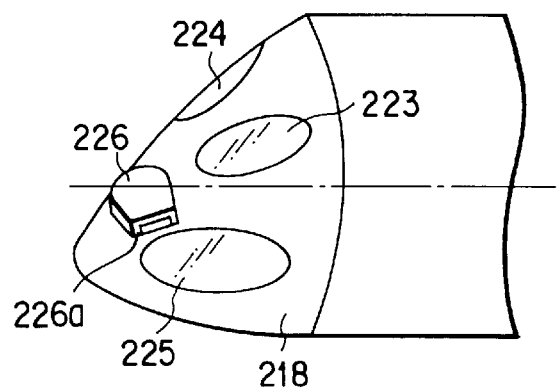
F I G. 16B

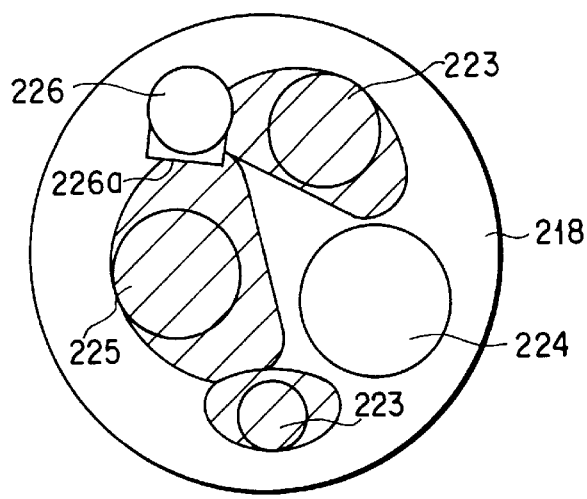
F I G. 19
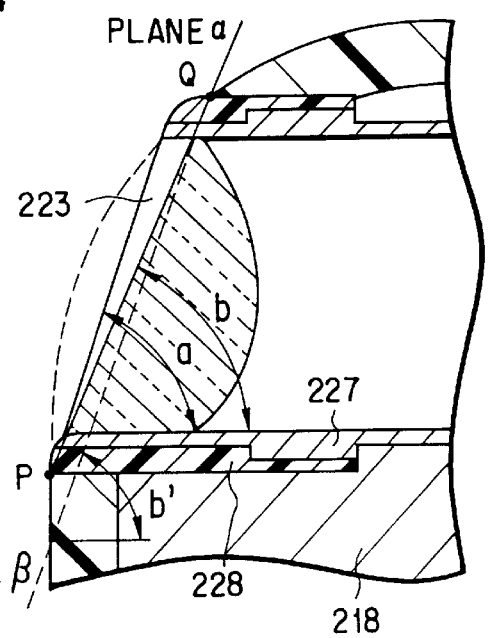
F I G. 20
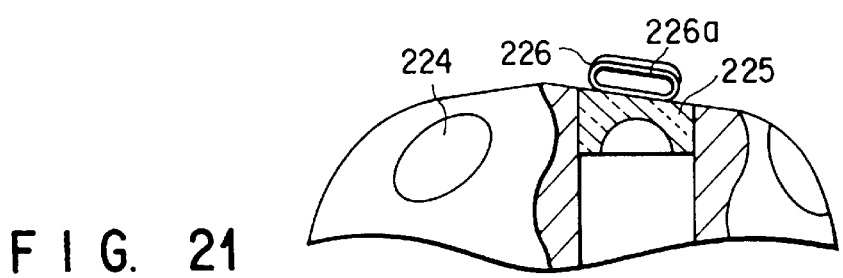
F I G. 21
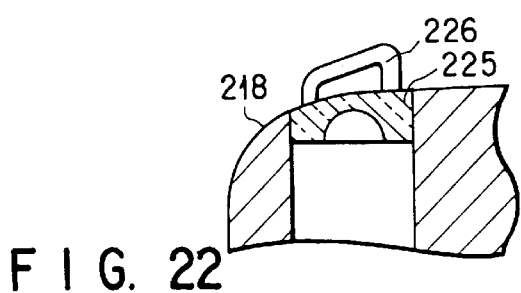
F I G. 22
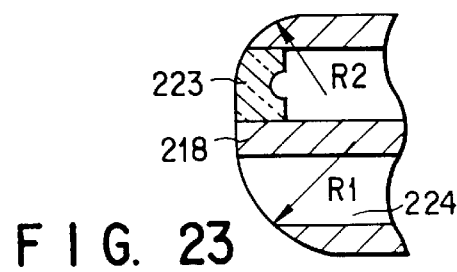
F I G. 23

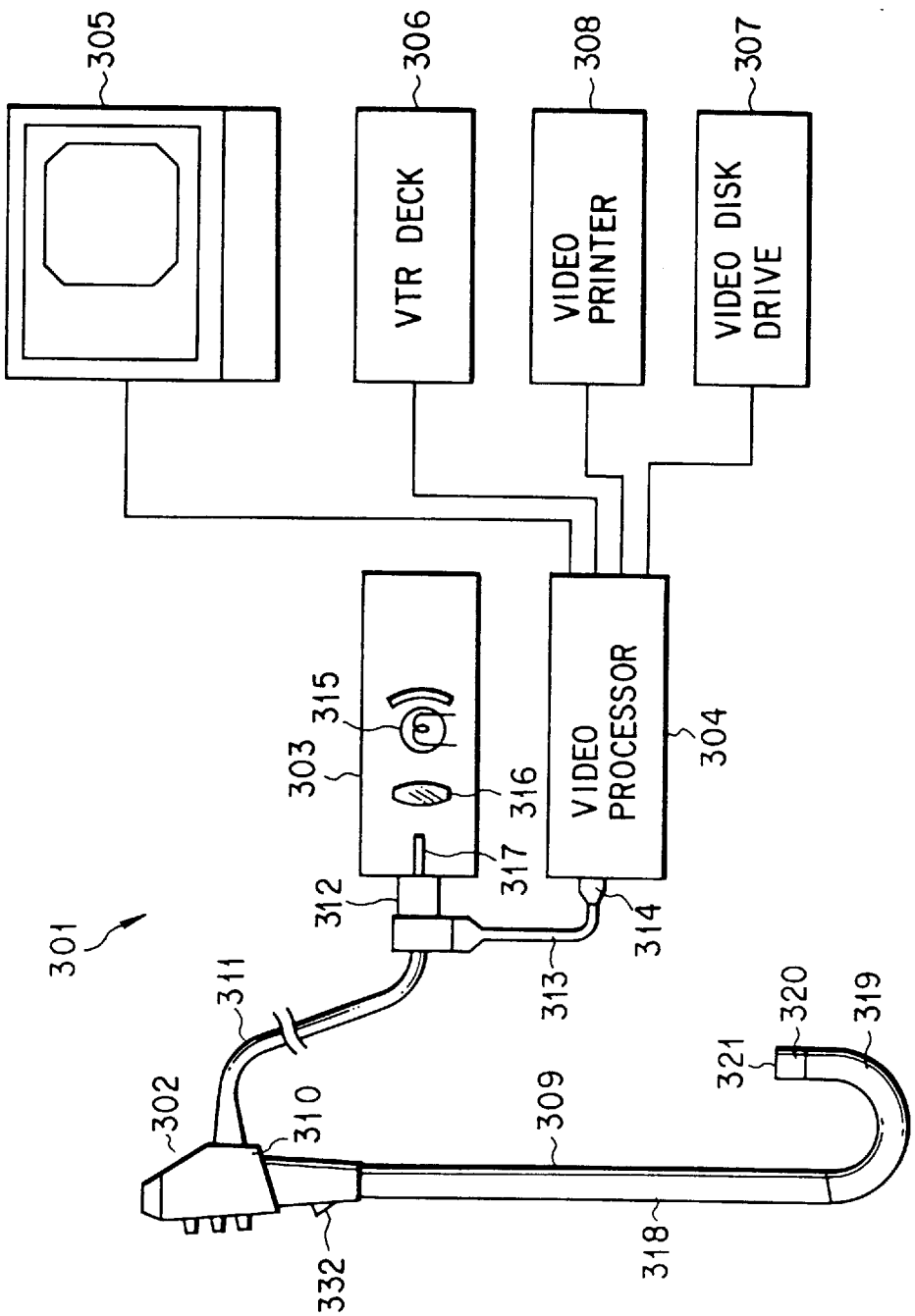
F I G. 28

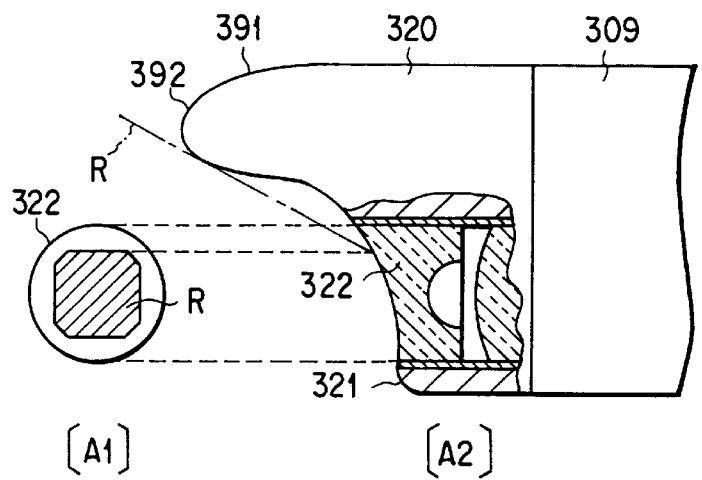
F I G. 31A
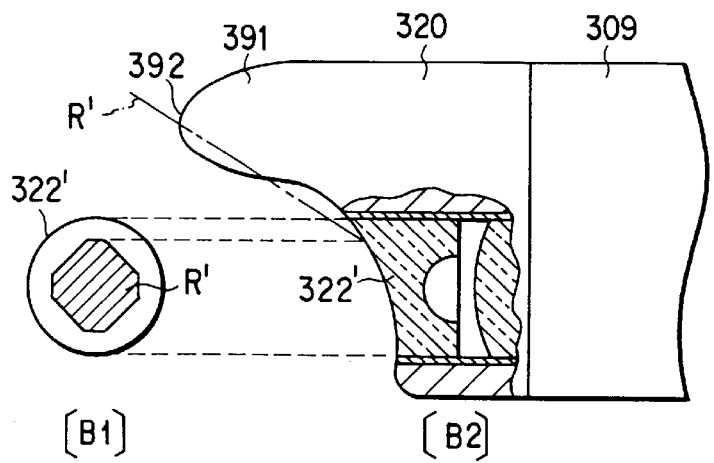
F I G. 31B
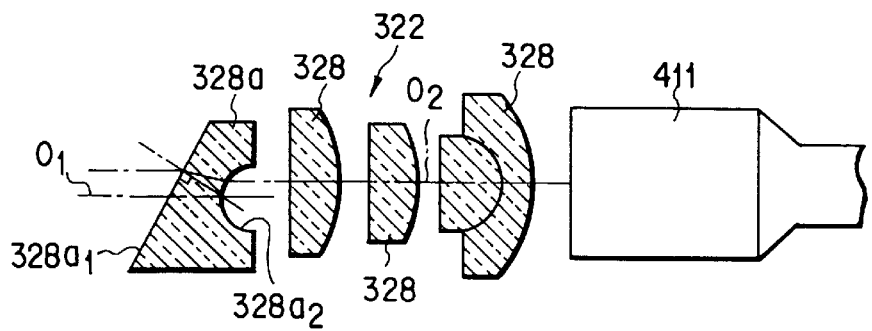
F I G. 32

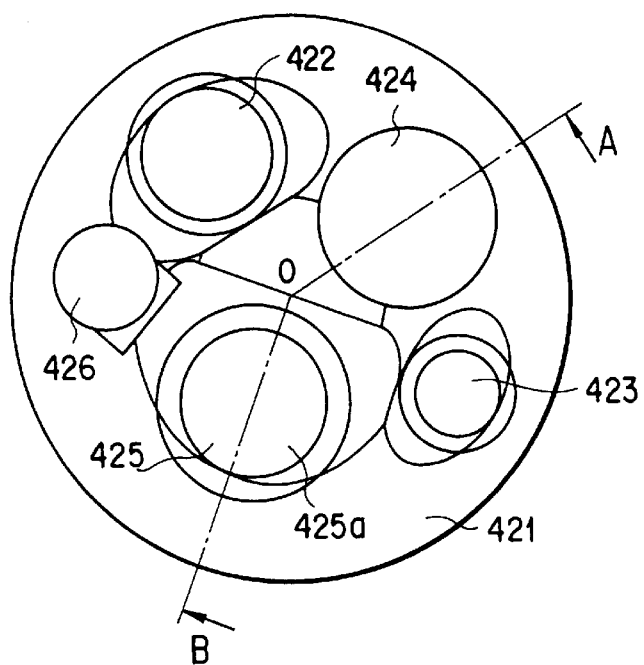
F I G. 36
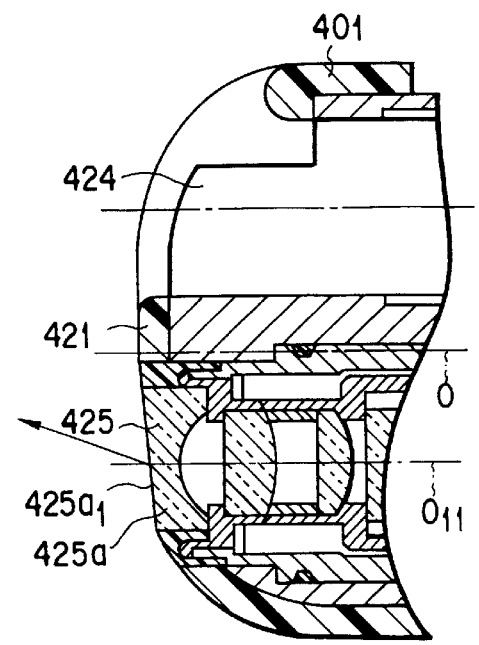
F I G. 37
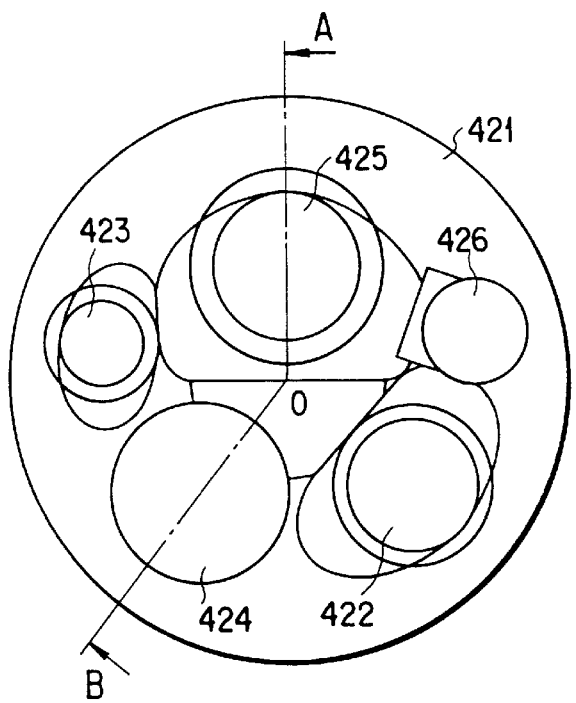
F I G. 38
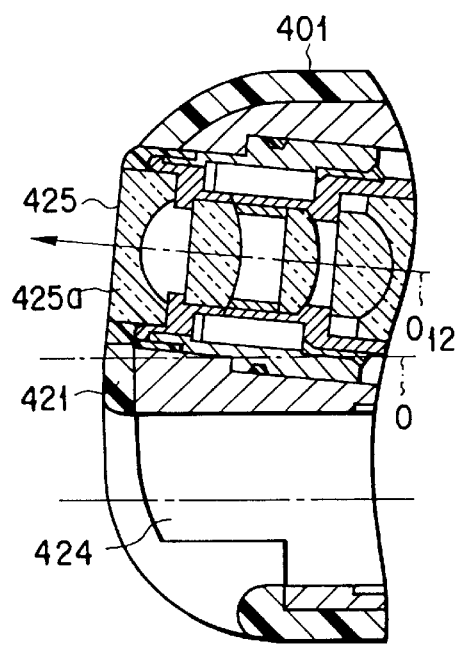
F I G. 39

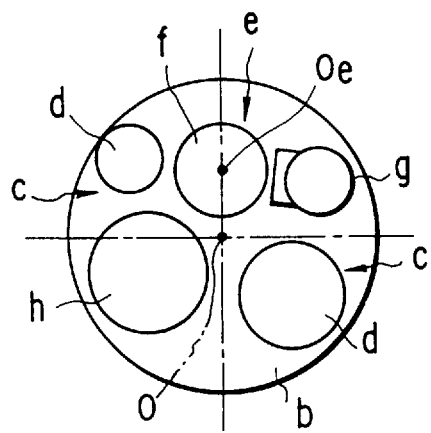
F I G. 41A
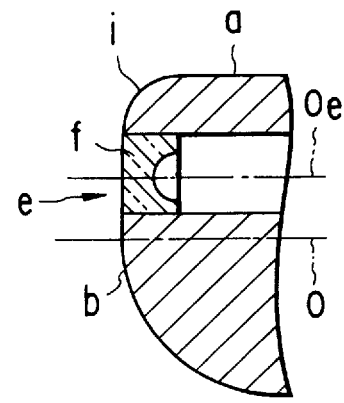
F I G. 41B
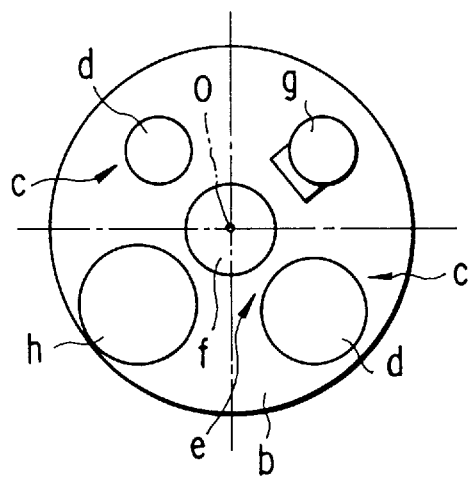
F I G. 41C
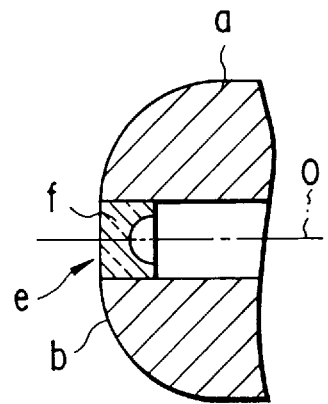
F I G. 41D

ENDOSCOPE

BACKGROUND OF THE INVENTION

1. Field of the Invention

The present invention relates to an endoscope for medical use.

2. Description of the Related Art

Generally, an endoscope for medical use comprises an insertion section and an operation section. The insertion section is designed to be inserted into a patient's body cavity. The operation section is coupled to the proximal end of the insertion section.

FIGS. 41A and 41B are front and sectional views of the distal portion (a) of the insertion section of the endoscope disclosed in Japanese UM Appln. KOKAI Publication No. 64-36816. As seen from FIGS. 41A and 41B, the distal portion (a) has front (b), in which an illumination window section (c) and an observation window section (e) are provided. The illumination window section (c) incorporates an illumination lens (d). The observation window section (e) incorporates an observation lens (f), a washing nozzle (g), a forceps channel (h) and the like.

As shown in FIG. 41B, the front (b) of the distal portion (a) is rounded. The observation lens (f) is fitted in the outermost part of the front (b). The light emitted through the illumination lens (d) is therefore prevented from reaching the observation lens (f). This eliminates the possibility that the image observed through the endoscope has flare or ghost. Since the front (b) is rounded, the distal portion (a) can be smoothly inserted into a body cavity.

In order to minimize the outside diameter of the distal portion (a), the illumination lens (d), observation lens (f), washing nozzle (g), forceps channel (h) and the like are arranged as close as possible to one another, as is illustrated in FIG. 41A. Consequently, the observation lens (f) is not aligned with the axis (O) of the distal portion (a). The outermost part of the rounded front (b), in which the lens (f) is fitted, is therefore located off the axis (O) namely aligned with the axis (Oe) of the observation lens (f). Consequently, the front (b) has a part (i) which has a radius of curvature less than any other part. This part (i) is more likely to be caught in the wall of a body cavity than any other part as the distal portion (a) is inserted into the body cavity. This would be a bar to smooth insertion of the insertion section.

To achieve smooth insertion of the insertion section, the front (b) of the distal portion (a) may be rounded as shown in FIG. 41D with a large radius (R) of curvature, having no part of a small radius of curvature. The front (b) can be so rounded by aligning the observation lens (f) with the axis (O) of the distal portion (a) as is shown in FIGS. 41C and 41D. If the lens (f) is aligned with the axis (O), however, the other components incorporated in the front (b), i.e., the illumination lens (d), washing nozzle (g), forceps channel (h) and the like, must be located around the observation lens (f) as shown in FIG. 41C. They are spaced apart from the lens (f) which is positioned at the center of the front (b). Consequently, the outer diameter of the distal portion (a) increases as is clearly seen from FIGS. 41A and 41B.

SUMMARY OF THE INVENTION

The present invention has been made in view of the forgoing. Its object is to provide an endoscope having a distal portion which has a relatively small outside diameter, which has a projection curved with a large radius of curvature and substantially uniformly along the entire circumference of the distal portion, and which can be smoothly inserted into a body cavity.

To attain the object, there is provided an endoscope having an insertion section to be inserted into a tubular cavity and an observation lens provided in a distal end of the insertion section and defining a view field perpendicular to an insertion direction of the insertion section. The endoscope comprises a rounded distal portion protruding from the distal end of the insertion section in the insertion direction of the insertion section. The observation lens is arranged so that it faces a portion of the rounded distal portion and so that a center of the observation lens is displaced from a forwardmost tip of the rounded distal portion.

Since the observation lens is positioned, with its center displaced from the forwardmost tip of the rounded distal portion, the components provided in the distal portion are arranged as close as possible to one another, and the distal portion is thinner than otherwise. Further, the distal portion is rounded with a large radius of curvature. Therefore, the insertion section can be inserted into a body cavity easily and smoothly.

The present invention can provide an endoscope which has a distal portion relatively thin and nonetheless rounded with a large radius of curvature, and which can therefore be inserted into a cavity easily and smoothly.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 1 is a block diagram showing a video endoscope system comprising an endoscope according to a first embodiment of the present invention;

FIG. 4 is a partially sectional view of the distal portion of an endoscope according to a third embodiment of the present invention;

FIG. 5 is a sectional view of the distal portion of an endoscope according to a fourth embodiment of the present invention;

FIG. 6A is a sectional view of the distal portion of an endoscope according to a fifth embodiment of the invention;

FIG. 6B is a sectional view of the distal portion of an endoscope according to a sixth embodiment of the present invention;

FIG. 14 is a front view of the distal portion of an endoscope which is a twelfth embodiment of this invention;

FIG. 15 is a front view of the distal portion of a modification of the endoscope shown in FIG. 14;

FIG. 16A is a front view showing the distal portion of an endoscope according to a thirteenth embodiment of the invention;

FIG. 16B is a side view of the distal portion illustrated in FIG. 16A;

FIG. 19 is a front view of the distal portion shown in FIG. 18;

FIG. 20 is an enlarged, longitudinal sectional view showing the end of the distal portion shown in FIG. 18;

FIG. 21 is a cutaway side view of the distal portion of an endoscope according to a sixteenth embodiment of the present invention;

FIG. 22 is a longitudinal sectional view of a modification of the distal portion shown in FIG. 21;

FIG. 23 is a longitudinal sectional view of the distal portion of an endoscope according to a seventeenth embodiment of the invention;

FIG. 28 is a block diagram illustrating a video endoscope system comprising an endoscope according to a twentieth embodiment of the invention;

FIG. 31A is a partially sectional side view of the distal portion of an endoscope according to a twenty-second embodiment of the invention;

FIG. 31B is also a partially sectional side view of the distal portion of the twenty-second embodiment, showing the rectangular view field which is positioned with one corner directed to the distal-end projection of the distal portion;

FIG. 32 is a side view of the observation lens unit incorporated in an endoscope according to a twenty-third embodiment of the invention;

FIG. 36 is a front view of the distal portion of an endoscope according to a twenty-seventh embodiment of the invention;

FIG. 37 is a sectional view of the distal portion, taken along line 37-O-37 in FIG. 36;

FIG. 38 is a front view of the distal portion of an endoscope according to a twenty-eighth embodiment of the invention;

FIG. 39 is a sectional view of the distal portion, taken along line 39-O-39 in FIG. 38;

FIG. 41A is a front view of the distal portion of the insertion section of a conventional endoscope;

FIG. 41B is a sectional view of the distal portion illustrated in FIG. 41A;

FIG. 41C is a front view of the distal portion of the insertion section of another conventional endoscope; and FIG. 41D is a sectional view of the distal portion shown in FIG. 41C.

DETAILED DESCRIPTION OF THE PREFERRED EMBODIMENTS

Figure 2A:
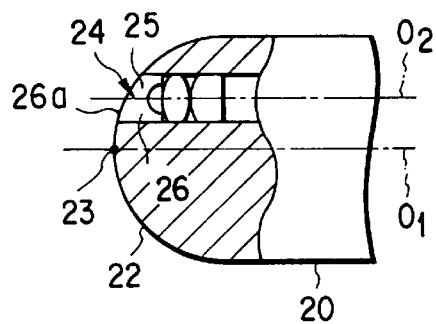
FIG. 2A is a partially sectional view of the distal portion of the endoscope shown in FIG. 1.

A video endoscope system 1 which comprises a video endoscope according to the first embodiment of the invention will be described with reference to FIG. 1. Although the first embodiment is a video endoscope, the present invention can be applied to an optical-fiber endoscope.

As shown in FIG. 1, the system 1 comprises an electronic endoscope 2, a light-source device 3, a video processor 4, a monitor 5, a VTR deck 6, a video disk drive 7 and a video printer 8. The electronic endoscope 2 comprises an insertion section 9 and an operation section 10. The insertion section 9 is designed to be inserted into a patient's body cavity. The operation section 10 is coupled to the proximal end of the insertion section 9.

A universal cord 11 is connected at one end to the operation section 10 and at the other end to a first connector unit 12. Connected to the connector unit 12 is one end of a signal cable 13. The other end of the cable 13 is connected to one end of a second connector unit 14. The connector units 12 and 14 are removably coupled to the light-source device 3 and the video processor 4, respectively.

The light-source device 3 contains a lamp 15, which emits light. The light is applied through a focusing lens 16 onto the light-receiving surface of the light guide 17 incorporated in the electronic endoscope 2. The light is guided through the light guide 17 to the distal end of the insertion section 9 and is applied outwards from the distal end.

Connected to the video processor 4 are the monitor 5, VTR deck 6, video disk drive 7 and video printer 8. The electronic endoscope 2 incorporates a charge coupled device (CCD) and a signal line. The charge coupled device converts an optical image into an electric signal. The signal is supplied via the signal line to the video processor 4. The video processor 4 processes the signal, generating image data. The image data is supplied to the monitor 5, which display the image represented by the image data. If necessary, the image data is supplied to the VTR deck 6, the video disk drive 7 and the video printer 8.

The insertion section 9 comprises a flexible tube 18, a bending portion 19 and a distal portion 20. The flexible tube 18 is coupled at the proximal end to the operation section 10 and at the distal end to the portion 19. The distal portion 20 is coupled to the distal end of the bending portion 19. The portion 19 can be bent and straightened under remote control of the operation section 10.

More specifically, the portion 19 can be bent upwards, downwards, leftwards and rightward as viewed from the front of the distal portion 20. Hereinafter, the four outer surface parts of the portion 19 which corresponds to the bending directions will be referred to as "upper side," "lower side," "left side," and "right side," respectively, for simplicity of description.

As shown in FIG. 2A, the distal portion 20 of the insertion section 9 has a rounded projection 22 at its distal end 21 (FIG. 1). The projection 22 has a semicircular cross section. The forwardmost tip 23 of the projection 22 is located substantially on the axis $O_1$ of the distal portion 20.

An observation window 24 is formed in the distal end 21 of the distal portion 20. The window 24 is located so that its axis $O_2$ is not aligned with the axis $O_1$ of the distal portion 20. Fitted in the window 24 is an observation lens unit 25. The unit 25 is comprised of a plurality of lenses. The foremost lens 26 of the lens unit 25 has a curved surface 26a which smoothly continues to the surface of the rounded projection 22, constituting part of the surface of the projection 22.

An illumination window (not shown) is formed in the distal end 21, too, and an illumination lens (not shown) is fitted in the illumination window. The observation lens 25, the illumination lens, a washing nozzle (not shown), a forceps channel (not shown) and the like are arranged as close as possible to one another in the distal end 21 of the distal portion 29, as in the conventional endoscope shown in FIGS. 41A and 41B. The forceps channel is coupled at its proximal end to the instrument port 27 of the operation section 10.

The endoscope 2 shown in FIGS. 1 and 2A is advantageous in the following respects.

First, the components provided in the distal end 21, i.e., the observation lens unit 25, illumination lens, washing nozzle, forceps channel and the like, can be arranged close to one another in the distal end 21, making it possible to reduce the outside diameter of the distal portion 20. This is because the observation lens unit 25 is located at any part of the distal end 21, except at the forwardmost tip 23 of the rounded projection 22.

Second, since the forwardmost tip 23 of the rounded projection 22 is located substantially on the axis $O_1$ of the distal portion 20, the projection 22 has a great radius R of curvature. Having a large radius of curvature, the projection 22 serves to insert the insertion section 9 into a body cavity more smoothly than with an endoscope wherein the tip 23 of the distal portion 20 is off the axis $O_1$, of the distal portion 20.

Third, since the foremost lens 26 of the observation lens unit 25 has a curved surface 26a which smoothly continues to the surface of the rounded projection 22, constituting part of the surface of the projection 22, the projection 22 can have a larger radius R of curvature than the case where the lens 26 protrudes from the surface of the projection 22.

Figure 2B:
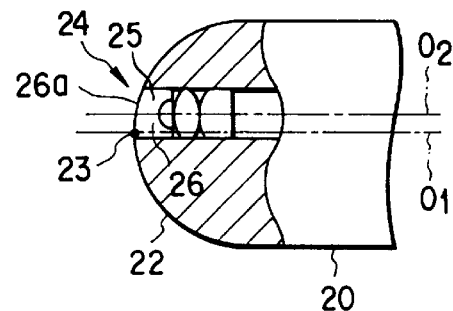
FIG. 2B is a partially sectional view of the distal portion of a first modification of the endoscope shown in FIG. 1.

FIG. 2B shows the distal portion 20 of a first modification of the first embodiment shown in FIG. 1. The first modification is different in that the observation lens unit 25 is positioned with its axis located closer to the axis $O_1$ of the portion 20. The first modification has the same advantages as the first embodiment.

Figure 2C:
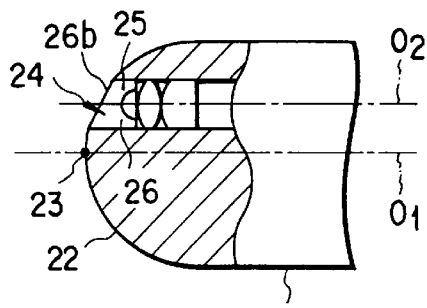
FIG. 2C is a partially sectional view of the distal portion of a second modification of the endoscope shown in FIG. 1.

FIG. 2C shows the distal portion 20 of a second modification of the first embodiment shown in FIG. 1. The second modification is different in that the foremost lens 26 of the lens unit 25 has a flat surface 26b inclined at such an angle that the surface 26b smoothly continues to the surface of the rounded projection 22, virtually constituting part of the surface of the projection. No steps are formed at the junction between the flat surface 26b of the lens 26 and the surface of the projection 22.

Obviously the inclined flat surface 26b of the lens 26 is more easy to form than the curved surface 26a which the lens 26 used in the first embodiment (FIG. 2A). It follows that the lens 26 can be made within a shorter time and at a lower cost than its counterpart of the first embodiment.

Figure 3A:
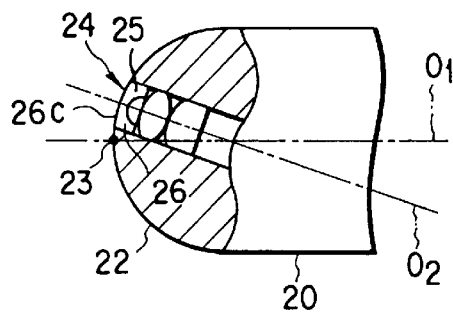
FIG. 3A is a partially sectional view of the distal portion of an endoscope according to a second embodiment of the invention.

FIG. 3A shows an endoscope according to the second embodiment of the invention. More precisely, it is a partially sectional view of the distal portion of the second embodiment. The second embodiment differs from the first embodiment in that the observation lens unit 25 is positioned with its axis $O_2$ inclined to the axis $O_1$ of the distal portion 20. The axis $O_2$ intersects at right angle with the tangent to the curved surface of the rounded projection 22 of the distal portion 20.

The foremost lens 26 of the observation lens unit 25 is a convex lens which is symmetrical to the optical axis. Its outer curved surface 26c constitute part of the curved surface of the rounded projection 22. Hence, the surface 26c smoothly continues to the surface of the projection 22.

The endoscope shown in FIG. 3A is advantageous in that the outer curved surface 26c of the foremost lens 26 is easy to form. This is because the lens 26 is a convex lens which is symmetrical to the optical axis. The lens 26 can therefore be manufactured within a shorter time and at a lower cost than the lens 26 used in the first embodiment (FIG. 2A), whose curved surface 26a is asymmetrical to the optical axis. In addition, the image observed through the endoscope would not be distorted asymmetrically to the optical axis of the observation lens unit 25.

Figure 3B:
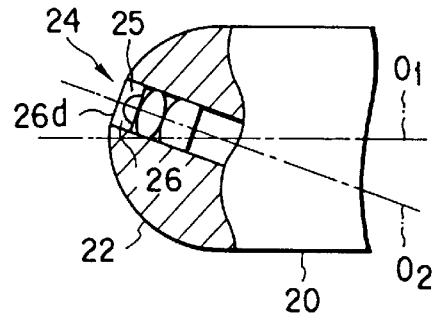
FIG. 3B is a partially sectional view of the distal portion of a modification of the endoscope shown in FIG. 3A.

FIG. 3B illustrates a modification of the endoscope shown in FIG. 3A. The modified endoscope is different in that the foremost lens 26 of the lens unit 25 is a flat lens which has surfaces symmetrical to the optical axis. Though flat, the surface 26d of the foremost lens 26 smoothly continues to the surface of the rounded projection 22, virtually constituting part of the surface of the projection. No steps are formed at the junction between the flat surface 26d of the lens 26 and the curved surface of the projection 22.

The modified endoscope shown in FIG. 3B is advantageous over the second embodiment (FIG. 3A) in two respects. First, the lens 26 can be manufactured within a shorter time and at a lower cost because it is a flat lens having surfaces symmetrical to the optical axis. Second, the image observed through the modified endoscope would not be distorted at all.

Another endoscope which is the third embodiment of the invention will be described with reference to FIG. 4. As seen from FIG. 4, the third embodiment differs from the first embodiment (FIG. 2A) in that a washing nozzle 41 extends near and along the axis $O_1$ of the rounded projection 22. The nozzle 41 has its distal end located afore the front surface 26a of the foremost lens 26 of the observation lens unit 25 and has its outlet port 42 located in front of the front surface 26a of the foremost lens 26. When a washing fluid is sprayed from the outlet port 42, washing clean the front surface 26a of the foremost lens 26, the endoscope acquires a view field.

The endoscope (FIG. 4) according to the first embodiment has the following advantages.

There is no possibility that the washing nozzle 41 protrudes from the circumferential surface of the distal portion 20, since the nozzle 41 extends near and along the axis $O_1$ of the rounded projection 22. Therefore, the nozzle 41 would not be caught in the wall of a narrow body cavity as the distal portion 20 is guided through the body cavity. This ensures smooth insertion of the distal portion 20 into the narrow body cavity.

Should the distal portion 20 have a projection extending outwards from the outer circumferential surface and be inserted into a cavity which has a diameter substantially equal to the outside diameter of the portion 20, the projection would be caught in the wall of the cavity, making it impossible for the insertion section to be inserted into the body cavity. Without such a projection, the distal portion 20 helps to achieve smooth and safe insertion of the insertion section.

The washing nozzle 41 need not be positioned to have its axis aligned the axis $O_1$ of the with the rounded projection 22. Rather, it suffices to position the nozzle 41 with respect to the axis $O_1$ of the projection 22 such that the outlet port 42 of the nozzle 41 is located in front of the front surface 26a of the foremost lens 26. As long as the nozzle 41 is so positioned, the distal portion 20 can serve to accomplish smooth and safe insertion of the insertion section.

Still another endoscope which is the fourth embodiment of the invention will be described with reference to FIG. 5. As shown in FIG. 5, the fourth embodiment is characterized in two respects. First, the distal portion 20 of the insertion section 9 has a projection 71 on its distal end. Second, the foremost lens 26 of the observation lens unit 25 has its front surface 72 located behind the projection 71. The surface 72 of the lens 26 is flat and inclined to the optical axis of the observation lens unit 25. The lens 26 has a view-field direction P. The direction P is inclined toward the projection 71 and to the direction in which the insertion portion 9 is inserted into a body cavity, because of the law of light refraction. Hence, any object present in front of the projection 71 can be observed through the endoscope. In other words, an object can be seen through the endoscope if it is located in a line passing the projection and extending parallel to the inserting direction of the section 9.

The distal end of the portion 20 is curved, smoothly continuing to the surface 72 of the foremost lens 26 of the observation lens unit 25.

The endoscope (FIG. 5) according to the fourth embodiment has the following advantages.

Since the projection 71 provided at the distal end of the portion 20 narrows toward its tip, the portion 20 be more easily guided into a narrow body cavity than otherwise. To be more specific, the tip of the projection 71 first enters the cavity. As the projection 71 is gradually moved forwards, the cavity is expanded. The distal portion 20 can therefore be smoothly inserted into the body cavity. The projection 71, which narrows toward its tip, serves to accomplish smooth insertion of the insertion section 9 into a body cavity, such as the pharynx or the pylorus, which has a relatively small diameter substantially equal to the outside diameter of the distal portion 20.

Generally, the optical axis of a lens having an inclined surface bends at the inclined surface as is illustrated in FIG. 5. In this regards it should be noted that the surface 72 of the foremost lens 26 is inclined to the optical axis of the observation lens unit 25, which is located near the projection 71 and parallel to the axis of the distal portion 20. The view field of the endoscope is therefore located in front of the projection 71. Since the view field is so located, a surgeon observing the interior of the body cavity can easily understand the position of the projection 71.

The view-field direction P of the foremost lens 26 may be set so that a part of the projection 71 can be seen in the view field of the endoscope. In this case, the surgeon can more easily know the position of the projection 71. Knowing the position the projection 71 takes in the body cavity, the surgeon can guide the distal portion 20 in the body cavity, without bringing the projection 71 into contact with the wall of the cavity or pressing the projection 71 too hard onto the wall of the cavity. This ensures safe guiding of the distal portion 20 in the body cavity.

The surface 72 of the foremost lens 26 may be inclined such that the focal point of the lens 26 is located at a point where the view-field direction P of the lens 26 intersects with a line passing the tip of the projection 71 and extending parallel to the axis of the distal portion 20. If the surface 72 is so inclined, any object located at said point can be clearly observed. This makes it easy for the surgeon to grasp the direction in which the projection 71 is being moved forward.

An endoscope according to the fifth embodiment of the present invention will be described with reference to FIG. 6A. The fifth embodiment is characterized in several respects. First, the distal portion 20 of the insertion section 9 has a projection 81 on its distal end. Second, the foremost lens 26 of the observation lens unit 25 is a flat lens having surfaces symmetrical to the optical axis and has its front surface 82 located behind the projection 81. Further, the observation lens unit 25 has its optical axis inclined to the axis of the distal portion 20 such that the view-field direction P of the foremost lens 26 inclines away from the axis of the projection 81.

The endoscope (FIG. 6A) according to the fifth embodiment has the following advantages.

As mentioned above, the optical axis of the foremost lens 26 of the observation lens unit 25 is inclined away from the projection 81 and also away from the direction of inserting the distal portion 20 into a body cavity. Thus, the view-field direction P of the lens 26 inclines away from the axis of the projection 81. Hence, a part of the projection 81 does not appear in the view field of the endoscope to narrow the view field as in the case where the optical axis of the lens 26 extends in the same direction as the direction of inserting the distal portion 20 into a body cavity.

Another endoscope which is the sixth embodiment of the present invention will be described with reference to FIG. 6B. The sixth embodiment is characterized in several respects. First, the distal portion 20 of the insertion section 9 has a forceps channel 91. Second, the front surface 92 of the foremost lens 26 is flat and inclined to the optical axis of the observation lens unit 25; the view-field direction P of the lens 26 is inclined toward the direction in which the insertion section 9 is inserted into a body cavity and toward the axis of the forceps channel 91. Thirdly, the distal end of the portion 20 is curved, smoothly continuing to the surface 92 of the foremost lens 26 of the observation lens unit 25.

The endoscope (FIG. 6B) according to the sixth embodiment has the following advantages.

The forceps protruding from the channel 91 can be seen in the view field of the endoscope, because the view-field direction P of the lens 26 is inclined toward the axis of the forceps channel 91. The surgeon can therefore know the direction and distance in and for which the forceps is moved in the body cavity and understand the distance between the tip of the forceps and the wall of the body cavity. The surgeon could not know the direction and distances if the view-field direction P of the lens 26 were almost identical to the direction in which the forceps is moved.

In addition, the forceps can be clearly observed in the view field of endoscope, greatly helping the surgeon to guide the forceps to an object that should be treated. This is because the front surface 92 of the foremost lens 26 is inclined at such an angle that the focal point of the lens 26 is located in front of the distal portion 20, at a point where the view-field direction P intersects with the axis of the forceps channel 91 line passing the tip of the projection 71 and extending parallel to the axis of the distal portion 20.

A video endoscope system 101 which comprises a video endoscope according to the seventh embodiment of the invention will be described with reference to FIGS. 7, 8A and 8B. The seventh embodiment is a video endoscope, but the present invention can be applied to an optical-fiber endoscope, as well.

Figure 7:
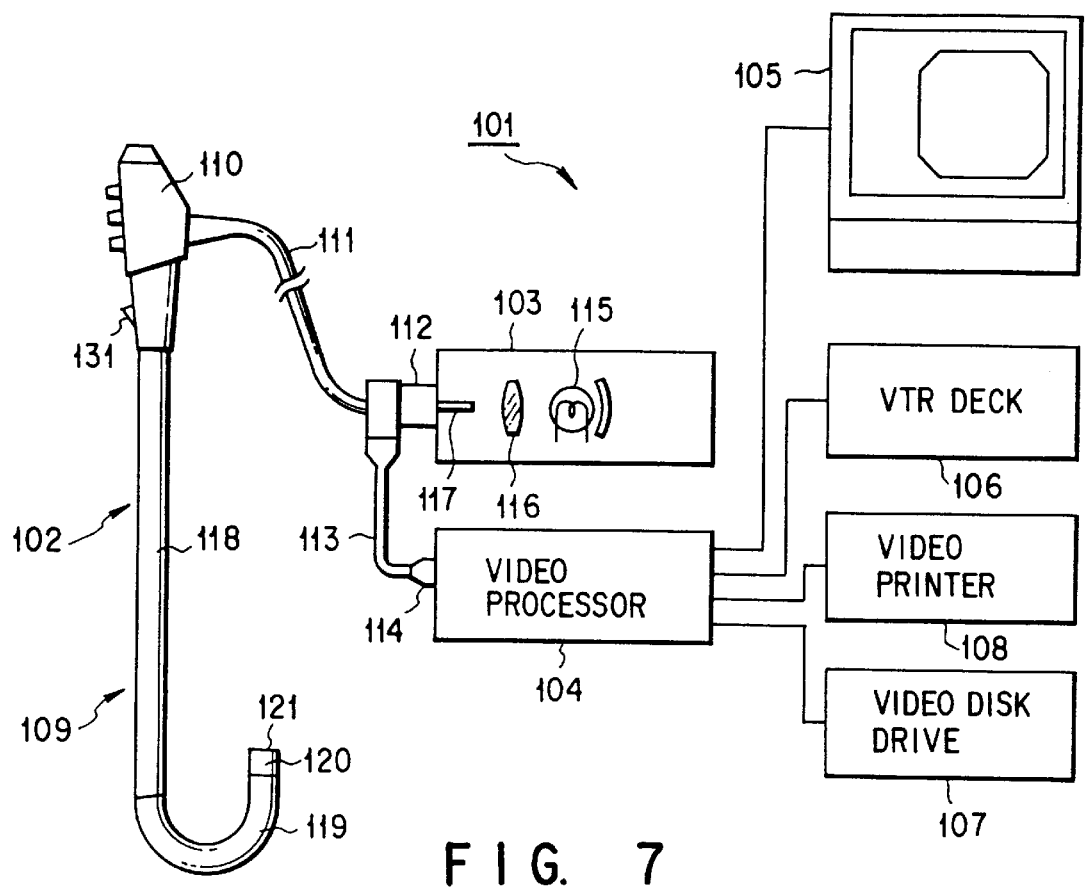
FIG. 7 is a block diagram illustrating a video endoscope system comprising an endoscope according to a seventh embodiment of this invention.

As shown in FIG. 7, the system 101 comprises an electronic endoscope 102, a light-source device 103, a video processor 104, a monitor 105, a VTR deck 106, a video disk drive 107 and a video printer 108. The electronic endoscope 102 comprises an insertion section 109 and an operation section 110. The insertion section 109 is designed to be inserted into a patient's body cavity. The operation section 110 is coupled to the proximal end of the insertion section 109.

A universal cord 111 is connected at one end to the operation section 110 and at the other end to a first connector unit 112. Connected to the connector unit 112 is one end of a signal cable 113. The other end of the cable 113 is connected to one end of a second connector unit 114. The connector units 112 and 114 are removably coupled to the light-source device 103 and the video processor 104, respectively.

The light-source device 103 contains a lamp 115, which emits light. The light is applied through a focusing lens 116 onto the light-receiving surface of the light guide 117 incorporated in the electronic endoscope 102. The light is guided through the light guide 117 to the distal end of the insertion section 109 and is applied outwards from the distal end.

Connected to the video processor 104 are the monitor 105, VTR deck 106, video disk drive 107 and video printer 108. The electronic endoscope 102 incorporates a charge coupled device (CCD) and a signal line. The imaging device converts an optical image into an electric signal. The signal is supplied via the signal line to the video processor 104. The video processor 104 processes the signal, generating image data. The image data is supplied to the monitor 105, which display the image represented by the image data. If necessary, the image data is supplied to the VTR deck 106, the video disk drive 107 and the video printer 108.

The insertion section 109 comprises a flexible tube 118, a bending 119 and a distal portion 120. The flexible tube 118 is coupled at the proximal end to the operation section 110 and at the distal end to the tube 119. The distal portion 120 is coupled to the distal end of the bending tube 119. The tube 119 can be bent and straighten under remote control of the operation section 110.

Figure 8A:
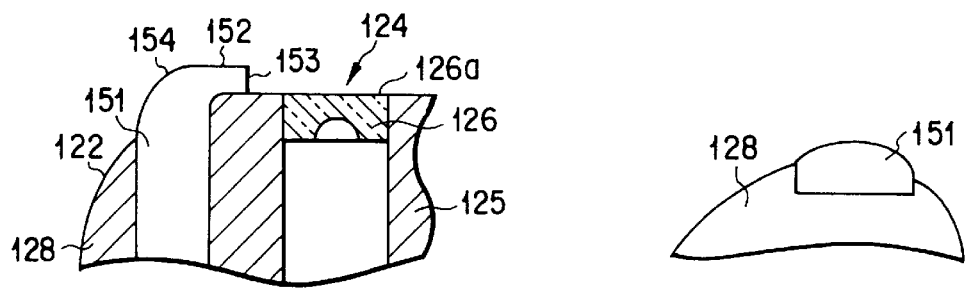
FIG. 8A is a sectional view of the distal portion of the endoscope shown in FIG. 7.

As shown in FIG. 8A, the distal portion 120 of the insertion section 109 has a curved surface 122 at its distal end 121 (FIG. 7). An observation window 124 is opens in the center part of the curved surface 122. Provided in the window 124 is an objective lens unit 125. The unit 125 comprises an observation lens 126 and a frame holding the lens 126. The observation lens 126 is a convex lens which is symmetrical to the optical axis.

A washing nozzle 151 is provided in the main body 128 of the distal portion 120. The nozzle 151 is designed to applying a washing solution onto the front surface 126a of the observation lens 126. The washing nozzle 151 is not integral with the main body 128 of the distal portion 120.

The washing nozzle 151 has an L-shaped distal end portion 152, which extends to a point located in front of the curved surface 122 of the distal portion 120 as shown in FIG. 8A. The L-shaped distal end portion 152 has an outlet port 153 which is directed to the front surface 126a of the observation lens 126.

The L-shaped distal end portion 152 of the washing nozzle 151 has curved surface 154 which is almost identical in shape to the curved surface 122 of the distal portion 120. As long as the nozzle 151 remains attached to the distal portion 120, the curved surface 154 smoothly continues to the curved surface 122 of the distal portion 120.

The endoscope (FIGS. 8A and 8B) according to the seventh embodiment has the following advantages.

First, the L-shaped distal end portion 152 of the washing nozzle 151 is not caught in the wall of a body cavity as the insertion section 109 is inserted into the body cavity. This is because the distal end portion has a curved surface 154 which is virtually identical in shape to, and thus smoothly continues to, the curved surface 122 of the distal portion 120.

It is required that the washing nozzle 151 protrude as much as possible from the distal end of the main body 128 of the distal portion 120 in order to apply the washing solution onto the front surface 126a of the observation lens 126. It is also required that the nozzle 151 protrude as little as possible from the distal end of the main body 128 in order to prevent the distal end portion 152 from being caught in the wall of the body cavity. To satisfy both requirements, the main body 128 of the distal portion 120 is rounded, having the curved surface 122, and the distal end portion 152 of the nozzle 151 is rounded, having the curved surface 154 almost identical to the curved surface 122.

Second, the washing nozzle 151 can be removed from the main body 128 of the distal portion 120 since the washing nozzle 151 is not integral with the main body 128 of the distal portion 120. Hence, the nozzle 151 can be readily replaced by a new washing nozzle, if it is clogged after a long use.

Figure 8B:
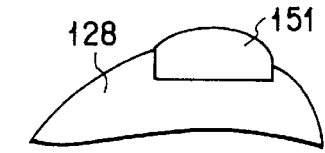
FIG. 8B is a side view of that part of the distal portion shown in FIG. 8A in which a washing nozzle is provided.

Third, the L-shaped distal end portion 152 can easily be manufactured to have a curved surface 154, simply because the curved surface 154 needs only to continue smoothly to the curved surface 122 of the distal portion 120 when viewed from any directions, for example from one side as shown in FIG. 8A and from another side as illustrated in FIG. 8B. In other words, the surface 154 of the distal end portion 152 is curved three-dimensionally. This greatly helps accomplish smooth and safe insertion of the insertion section 109 into a body cavity.

Figure 8C:
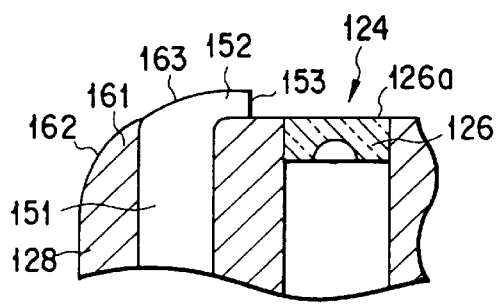
FIG. 8C is a sectional view of the distal portion of an endoscope which is an eighth embodiment of this invention.

An endoscope which is the eighth embodiment of the invention will be described with reference to FIG. 8C. As seen from FIG. 8C, the eighth embodiment is characterized in that the main body 128 of the distal portion 120 has a rounded portion 161. The portion 161 protrudes forwards as much as the distal end portion 152 of the washing nozzle 151 and has a curved surface 162. Further, the distal end portion 152 of the nozzle 151 has a curved surface 163 which smoothly continues to the curved surface 162 of the rounded portion 161 of the main body 128. Thus, as long as the nozzle 151 remains attached to the distal portion 120, the curved surface 162 of the portion 161 smoothly continues to the curved surface 163 of the distal end portion 152 of the washing nozzle 151.

The endoscope (FIG. 8C) according to the eighth embodiment is advantageous in the following respects.

First, the insertion section 109 can be inserted into a body cavity, more smoothly and, hence, more safely than that of the seventh embodiment (FIGS. 8A and 8B). This is because the distal end portion 152 of the nozzle 151 has a curved surface 163 which very smoothly continues to the curved surface 162 of the rounded portion 161 of the main body 128.

Furthermore, as in the seventh embodiment, the washing nozzle 151 can be removed from the main body 128 of the distal portion 120 since the washing nozzle 151 is a component integral with the main body 128 of the distal portion 120. Thus, the nozzle 151 can be readily replaced by a new washing nozzle, if it is clogged after a long use.

Figure 8D:
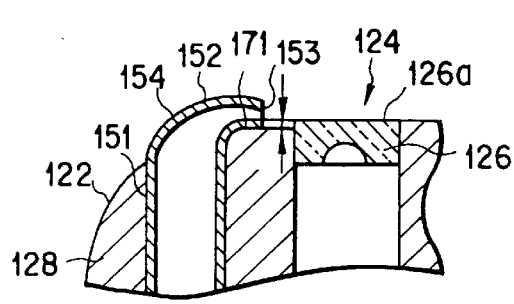
FIG. 8D is a sectional view of the distal portion of an endoscope which is a ninth embodiment of the present invention.

An endoscope which is the ninth embodiment of this invention will be described, with reference to FIG. 8D.

The ninth embodiment differs from the seventh embodiment (FIGS. 7, 8A and 8B) in that part 171 of the distal surface of the main body 128, at which the washing nozzle 151 is provided,, recedes from the other part of the distal surface by, at most, the wall thickness t of the washing nozzle 151. Nonetheless, the outlet port 153 of the nozzle 151 does not recede from the distal surface of the main body 128.

Provided on the receded part 171 of the distal surface of the main body 128, the L-shaped distal end portion 152 of the washing nozzle 151 protrudes less from the main body 128 than otherwise. Furthermore, since the outer curved surface of the distal end portion 152 smoothly continues to the curved surface 122 of the distal portion 120, the main body 128 of the distal portion 120 is not likely to be caught in the wall of a body cavity. This serves to achieve smooth and safe insertion of the insertion section 109 into a body cavity.

The seventh, eighth and ninth embodiments are not limited to endoscopes which have a washing nozzle bent at the distal end. Rather, they can be applied to endoscopes which have a washing nozzle whose distal end surface is curved and smoothly continues to the distal end surface of the insertion section.

Figure 9:
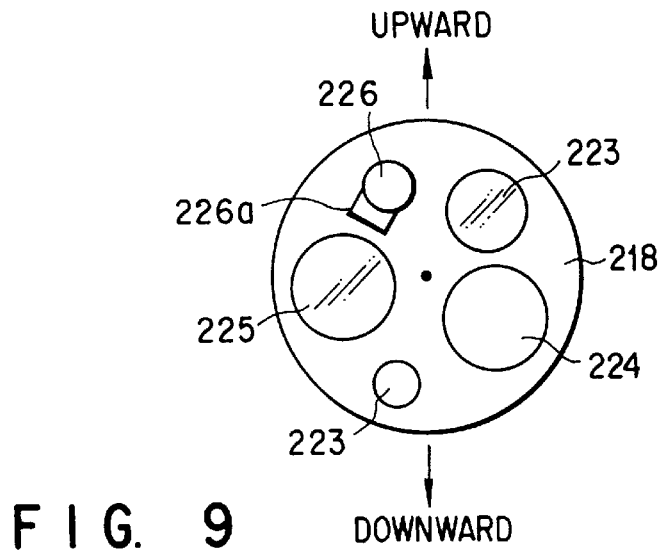
FIG. 9 is a front view of the distal portion of an endoscope which is a tenth embodiment of the invention.
Figure 10:
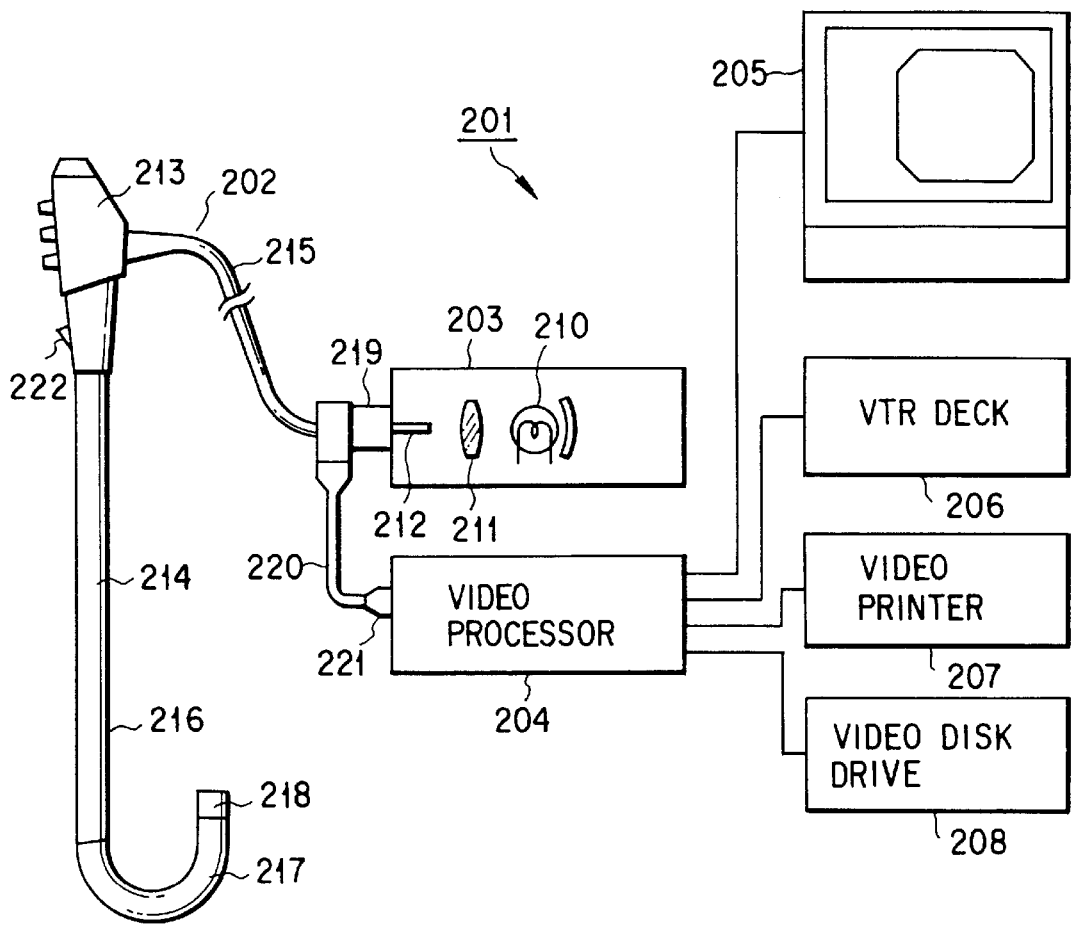
FIG. 10 is a block diagram showing a video endoscope system comprising an endoscope according to the tenth embodiment of the present invention.

A video endoscope system 201 which comprises a video endoscope according to the tenth embodiment of the invention will be described with reference to FIGS. 9 to 12. FIG. 9 is a front view of the distal portion of this endoscope, and FIG. 10 is a block diagram showing the video endoscope system comprising 201. The tenth embodiment is a video endoscope, but the present invention can be applied to an optical-fiber endoscope, as well.

As shown in FIG. 10, the system 201 comprises a video endoscope 202, a light-source device 203, a video processor 204, a monitor 205, a VTR deck 206, a video printer 207, and a video disk drive 208. The light-source device 203 incorporates a light source 210 and a focusing lens 211. The light emitted from the light source 210 is applied through the focusing lens 211 to an end of a light guide 212 held in the connector receptacle of the light-source device 203. (The light guide 212 will be described later.)

The video endoscope 202 comprises an operation section section 213, an insertion section 214 and a universal cord 215. The insertion section 214 comprises a flexible tube 216, a bending portion 217, and a distal portion 218. The distal portion 218 is connected to the distal end of the bending portion 217. A connector 219 is connected to one end of the universal cord 215. It is from the connector 219 that the light guide 212 extends. When the connector 219 is attached to the connector receptacle of the light-source device 203, the video endoscope 202 is optically connected to the light-source device 203.

Connected to the connector unit 219 is one end of a signal cable 220. The other end of the cable 220 is connected to one end of a connector 221, which is connected to the video processor 204.

A light guide fiber, an image guide fiber, an air/water supply channel, a forceps channel and the like, all not shown, are incorporated in the insertion section 214 of the video endoscope 202. The proximal end of the forceps channel communicates with an instrument insertion port 222 provided in the operation section 213.

The distal portion 218 will be described with reference to FIG. 9. As shown in FIG. 9, the distal portion 218 incorporates an illumination lens 223, a forceps-channel outlet port 224, an observation lens 225, and a washing nozzle 226. The lens 223 is optically connected to the light guide fiber mentioned above. The outlet port 224 communicates with the forceps channel. The observation lens 225 which functions as an observation window is optically connected to the image guide fiber. The washing nozzle 226 is designed to apply a washing solution onto the front surface of the observation lens 225. As shown in FIG. 9, the nozzle 226 assumes an upper-left position with respect to the axis O of the distal portion 218 and is located above the observation lens 225, as viewed from the front of the distal portion 218.

The nozzle 226 has its outlet port 226a directed to the front surface of the observation lens 225. That is, the washing nozzle 226 exists at a position near the lower peripheral edge of the distal portion 218, as viewed from the front of the distal portion 218.

How the video endoscope 202 is used will be explained, with reference to FIGS. 11 and 12.

Figure 11:
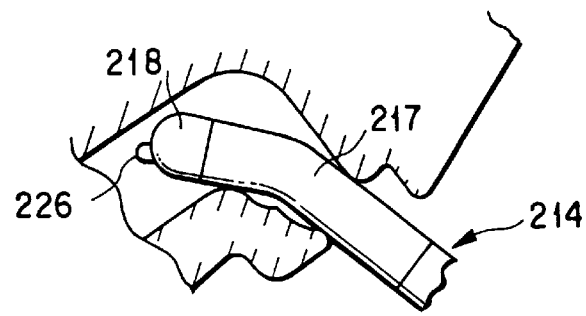
FIG. 11 is a diagram explaining how the insertion section of the endoscope shown in FIG. 10 is inserted into the esophagus through the mouth.
Figure 12:
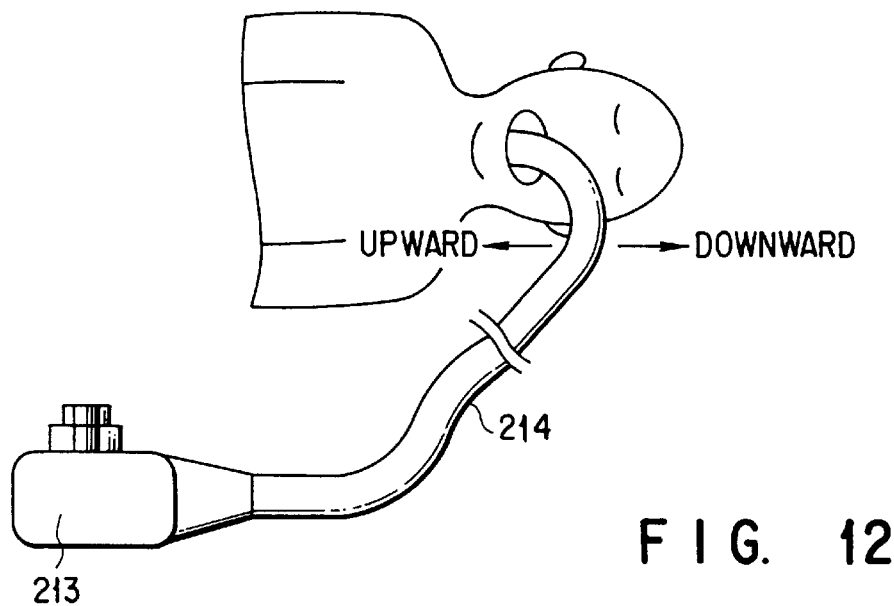
FIG. 12 is another diagram explaining how the insertion section of the endoscope shown in FIG. 10 is inserted into the esophagus through the mouth.

FIG. 11 illustrates how the insertion section 214 of the endoscope 202 (FIG. 10) is inserted into the esophagus through the mouth. First, a surgeon inserts the bending portion 217 into the esophagus through the mouth, while bending the portion 217 to the shape of the esophagus which extends from the throat to the stomach. In most cases, the operation section 213 is positioned horizontally and placed on the left side of the patient and the portion 217 is first directed from the left into the mouth, as is illustrated in FIG. 12.

To insert the insertion section 214 into the esophagus smoothly, the bending portion 217 is bent upwards as it is inserted into the throat. When the portion 217 is so bent, the distal portion 218 is located at the entrance to the throat. Since the portion 217 is bent upwards, the washing nozzle 226 does not touch the back wall of the throat.

In some cases, the operation section 213 is positioned vertically so that the surgeon may observe the interior of the esophagus. As the distal portion 218 is inserted into the throat, it contacts the back wall of he throat at its right side as viewed from the direction of insertion. In this case, the washing nozzle 226 does not touch the back wall of the throat if it is located at the left side of the bending portion 217.

If the endoscope 202 were an optical-fiber endoscope, the surgeon would position the operation section 213 vertically in most cases, in order to observe the interior of the esophagus. To prevent the washing nozzle 226 from touching the back wall of the throat, it would suffice to position the nozzle 226 at any side of the observation lens 225, but the right side thereof.

Therefore, the washing nozzle 226 provided at the distal end of the insertion portion 218 is not caught in the wall of the throat as the insertion portion 218 is inserted into the esophagus. In other words, the insertion section 214 of the video endoscope 202, i.e., the tenth embodiment of the invention, can be easily and smoothly inserted into a body cavity.

Figure 13:
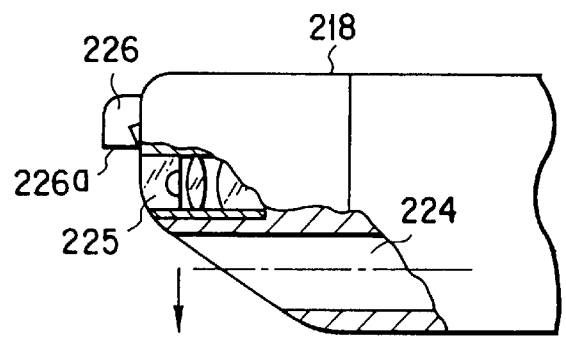
FIG. 13 is a partially sectional view of the distal portion of an endoscope according to an eleventh embodiment of the present invention.

An endoscope which is the eleventh embodiment of the present invention will be described, with reference to FIG. 13. FIG. 13 is a partially sectional view of the distal portion of the eleventh embodiment. The eleventh embodiment may be either an optical-fiber endoscope or an video endoscope.

If the eleventh embodiment is an optical-fiber endoscope, the right side of the distal portion 218 is curved or tapered toward such that it narrows toward the distal end as is illustrated in FIG. 13. The distal end 218 can be inserted into a body cavity more smoothly than otherwise. As shown in FIG. 13, the washing nozzle 226 is located on the distal end of the portion 218, close to the center thereof, not at the peripheral edge thereof. Hence, the nozzle 226 neither touches the back wall of the throat nor is caught in an inner wall of a narrow tubular organ as the distal portion 218 is guided through the throat or the the tubular organ.

If the eleventh embodiment is a video endoscope, both the lower side and right side of the distal portion 218 are curved or tapered toward such that it narrows toward the distal end. In this case, too, the distal end 218 can be inserted into a body cavity more smoothly than otherwise.

Another endoscope which is the twelfth embodiment of the invention will be described, with reference to FIG. 14. The components similar to or identical to those of the tenth embodiment (FIGS. 9 to 12) will be designated at the same reference numerals in FIG. 14 and will not be described in detail. FIG. 14 is a front view of the distal portion of the twelfth embodiment.

As shown in FIG. 14, the distal portion 218 incorporates an illumination lens 223, a forceps-channel outlet port 224, an observation lens 225, and a washing nozzle 226. The nozzle 226 has its outlet port 226a directed to the front surface of the observation lens 225. The washing nozzle 226 assumes a left position with respect to the axis of the distal portion 218 and is located above the observation lens 225, as viewed from the front of the distal portion 218.

Located at a left position with respect to the axis of the distal portion 218, the washing nozzle 226 is at a long distance from the lower side of the distal portion 218. As in the tenth embodiment, the washing nozzle 226 does not touch the back wall of the throat at all as the distal portion 218 is guided through the throat, when the bending portion 217 is bent upwards and inserted into the throat.

A modification of the twelfth embodiment will be described, with reference to FIG. 15 which is a front view of the distal portion 218 of the modified endoscope. The modified endoscope is characterized in that the washing nozzle 226 is located below the axis of the distal portion 218 at a short distance from the axis thereof. Also in this modification, the outlet port 226a of the nozzle 226 does not exists near the lower side of the distal portion 218. The modification of the twelfth embodiment can also attain the same advantages as the tenth embodiment shown in FIGS. 9 to 12.

Still another endoscope which is the thirteenth embodiment of this invention will be described, with reference to FIGS. 16A and 16B. The components similar or identical to those of the tenth embodiment (FIGS. 9 to 12) are denoted at the same reference numerals in FIGS. 16A and 16B and will not be described in detail.

As in the embodiment described above, the bending portion 217 be bent upwards, downwards, to the left, and to the right. FIG. 16A is a front view showing the distal portion of the thirteenth embodiment, and FIG. 16B is a side view thereof. As shown in FIG. 16B, the distal portion is rounded at its distal end. The nozzle 226 for applying a washing solution onto the front surface of the observation lens 225 is located below the axis of the distal portion 218 and above the rounded distal end.

Located above the rounded distal end, the washing nozzle 226 is not caught in the wall of the throat as the distal portion 218 is passed through the throat. This is because the lower side of the distal portion 218 does touch the back wall of the throat as the distal portion 218 inserted into the esophagus through the throat. Further, since the nozzle 226 is located far from the lower side of the distal portion 218 (that is, near the upper side thereof), the rounded distal end of the portion 218 prevents the nozzle 226 from contacting the back wall of the throat. In addition, since the distal end of the portion 218 is rounded, it is hardly be caught in the wall of the throat. This ensures smooth insertion of the insertion section 214 into the esophagus.

Moreover, the distal portion 218 expands a tubular organ as it is inserted deeper through the organ since its distal end gradually broaden toward the proximal end. This facilitates the insertion of the insertion section 214 into a narrow tubular organ. Although the washing nozzle 226 is located below the axis of the distal portion 218 as shown in FIG. 16B, the thirteenth embodiment can achieve the same advantages as the tenth embodiment, provided that the nozzle 226 is positioned above the rounded distal end of the portion 218.

Figure 17A:
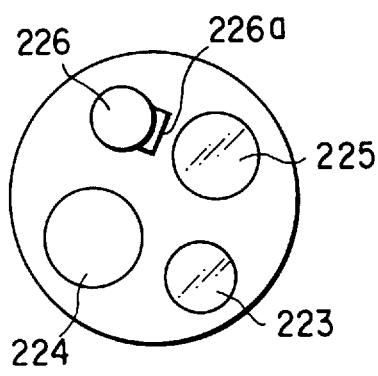
FIG. 17A is a front view showing the distal portion of an endoscope according to a fourteenth embodiment of this invention.
Figure 17B:
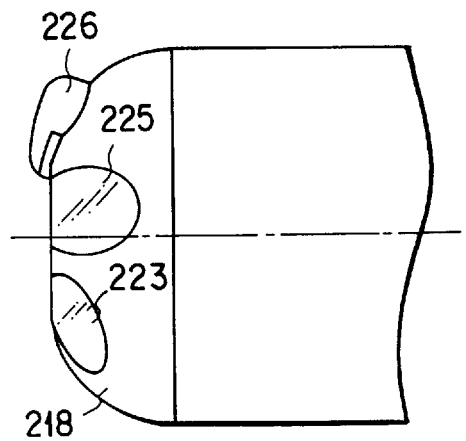
FIG. 17B is a side view of the distal portion illustrated in FIG. 17A.

The fourteenth embodiment of the invention, which is an endoscope, too, will be described with reference to FIGS. 17A and 17B. FIG. 17A is a front view of the distal portion 218 of this embodiment, and FIG. 17B is a side view thereof. In FIGS. 17A and 17B, the components similar or identical to those of the tenth embodiment (FIGS. 9 to 12) are designated at the same reference numerals. They will not be explained in detail in the following description.

As illustrated in FIG. 17A, the distal portion 218 incorporates an illumination lens 223, a forceps-channel outlet port 224, an observation lens 225, and a washing nozzle 226. As can be understood from FIG. 17B, the distal portion 218 has a peripheral edge rounded with a radius of curvature almost equal to the radius of the distal portion 218. As shown in FIG. 17A, the washing nozzle 226 is located above the axis of the distal portion 218 as viewed from the front of the portion 218.

Located above the axis of the distal portion 218, the washing nozzle 226 does not touch the back wall of the throat as the distal portion 218 is guided through the throat, when the bending portion 217 is bent upwards and inserted into the throat. There is no possibility that the nozzle 226 is caught in the wall of the throat, and the insertion section 214 can be smoothly inserted into a narrow tubular organ. Further, since the distal portion 218 has a rounded puerperal edge, it can be smoothly guided into the esophagus even if it touches the wall of the upper portion of the esophagus, as the bending portion 217 is inserted into the esophagus while bent to conform in shape to the tubular body cavity consisting of the throat and the esophagus. Thus, the fourteenth embodiment can attain the same advantages as the tenth embodiment.

Figure 18:
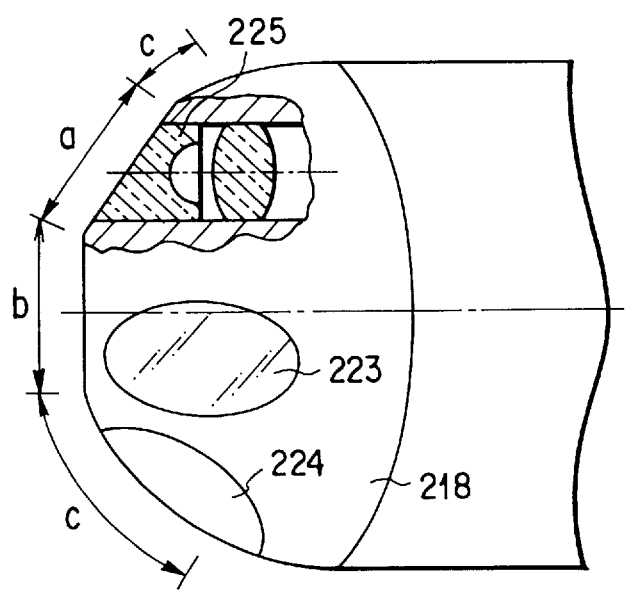
FIG. 18 is a cutaway perspective view of the distal portion of an endoscope according to a fifteenth embodiment of the invention.

The fifteenth embodiment of the invention, which is an endoscope, too, will be described with reference to FIGS. 18 to 20. FIG. 18 is a cutaway side view of the distal portion of the endoscope, FIG. 19 is a front view thereof, and FIG. 20 is an enlarged, longitudinal sectional view thereof. In FIGS. 18 to 20, the components similar or identical to those of the tenth embodiment (FIGS. 9 to 12) are designated at the same reference numerals. They will not be explained in detail in the following description.

As shown in FIG. 18, the distal portion 218 has a generally curved surface (c) and two flat surfaces (a) and (b). The flat surfaces (a) and (b) are inclined so that perpendiculars to them extend in different directions. In FIG. 19, the flat surfaces (a) and (b) are shown as shaded areas. As shown in FIG. 19, the distal portion 218 incorporates an illumination lens 223, a forceps-channel outlet port 224, an observation lens 225, and a washing nozzle 226. The lenses 223 and 225 have their front surfaces positioned substantially parallel to the flat surfaces (b) and (a), respectively. Thus, there are no stepped portions at the junctions between the distal portion 218 and the lenses 223 and 225. As shown in FIG. 20, the angle (a) at which the front surfaces of the lenses 223 and 225 incline to the axis of the distal portion 218 is a little larger than the angle (b) at which the surface (b) inclines to the axis of the portion 218.

Since the lenses 223 and 225, each being a wedge-shaped which can be made easily, have their front surfaces substantially parallel to the flat surfaces (b) and (a) of the distal portion 218, there are formed no stepped portions at the junctions between the distal portion 218 and the lenses 223 and 225. The surface (c) of the distal portion 218 is generally curved with a predetermined radius of curvature. As a result, no appearance of any part of the distal portion 218 in the view field of the endoscope, nor will filth accumulate at the junctions between the distal portion 218 and the lenses 223 and 225. The lenses 223 and 225 may be replaced by flat lenses each having surfaces symmetrical to the optical axis. If this is the case, the lenses 223 and 225 only need to be positioned with their axes perpendicular to the flat surfaces (b) and (a), respectively.

The lenses 223 and 225 are set in the distal portion 218, with their foremost parts aligned with the foremost parts of the flat surfaces (b) and (a), filth or water is less likely to accumulate on the lenses 223 and 225. Generally, the larger the angle between the incidence surface of a lens and the optical axis thereof, the less the distortion of the image observed trough the lens. Since the angle (a) between the outer face of the illumination lens 223 and the optical axis of the lens 223 is a little less than 90°, the image o observed through the lens 223 is distorted but a very little. The same can said of the observation lens 225.

FIG. 20 is a sectional view, taken along a plane in which exist the optical axis of the illumination lens 223 and the foremost part of the distal portion 218. Shown in FIG. 20 are points P and Q at which the upper and lower edges of the hole accommodating the lens 223 are located on the surface of the distal portion 218. The flat surface (b) in which the lens 223 is located as shown in FIG. 19 can therefore be small, and the surface c of the distal portion 218 is generally curved. Therefore, the distal portion 218 can be smoothly inserted into a body cavity. If point Q is moved toward the foremost part of the distal portion 218, surface (b) will be a plane β. In this case, the angle (b') between the plane β and the axis of the distal portion 218 is greater than the angle (b) at which the surface (b) inclines to the axis of the portion 218. Obviously, and approaches 90°. The distortion of the image observed through the lens 223 is less than otherwise.

The front surfaces of both lenses 223 and 225 smoothly continue to the curved surface (c), though they are flat surfaces. The distal end of the portion 218 is therefore generally a curved surface. The distal end 218 can be smoothly inserted into a body cavity, with no filth accumulated on the distal portion 218 no appearance of any part of the distal portion 218 in the view field of the endoscope.

As is clearly shown in FIG. 20, a part of the curved front of the distal portion 218 is flat, and the front surfaces of both lenses 223 and 225, which are wedge-shaped are inclined to a plane perpendicular to this axes and smoothly continue to the curved surface front of the distal portion 218. Shown in FIG. 20 is a frame 227 which holds the illumination lens 223. The distal end of the frame 227 is inclined, substantially parallel to the front surface of the lens 223.

As shown in FIG. 20, the frame 227 has an annular projection on its circumferential surface. The frame 227 has such a length and is so inclined at the distal end that its distal end does not project from the distal end of the portion 218 once the frame 227 has been fitted in the distal portion 218.

The illumination lens 223 is fitted in the frame 227, taking a prescribed position in the distal portion 218. The frame 227 protects the lens 223 and prevents a liquid from leaking into the illumination lens unit. Since the frame 227 has an inclined distal end which substantially parallel to the front surface of the lens 223, it holds the entire thick portion of the lens 223, in both airtight and watertight fashion. The lens 223 could not be held in such a fashion if the distal end of the frame 227 were perpendicular to the axis of the distal portion 218 as a lens frame for holding a lens having surfaces symmetrical to the optical axis and should inevitably be aligned with the distal end of the thin portion of the lens 223.

Generally it is desired the a lens frame has a distal end positioned almost in flush with the distal end of the front surface of the lens, in order to hold the lens steadfastly and prevent a liquid from leaking into the lens unit. Here arises a problem. The frame 227 is made of metal as in most cases. If the distal end of the frame 227 and a medical instrument protruding from the distal end of the portion 218 contact the wall of a body cavity, an electric current will flow between the frame 227 and the instrument through the wall of the body cavity. Consequently, the wall of the body cavity will be damaged. To avoid this accident, the frame 227 is covered with an electrically insulating adhesive 228. As seen from FIG. 20, the lens frame 227 has its distal end set substantially in flush with the outer surface of the lens 223. Hence, it holds the lens 223 more firmly than in the case its distal end is in a plane perpendicular to its axis.

The endoscope according to the fifteenth embodiment (FIGS. 18 to 20) is advantageous in that the frame 227 holds the lens 223 steadfastly and prevents a liquid from leaking into the lens unit since its distal end is inclined, extending substantially parallel to the inclined front surface of the lens 223.

An endoscope according to the sixteenth embodiment of the invention, with reference to FIG. 21. FIG. 21 is a cutaway side view of the distal portion 218 of the sixteenth embodiment. The components similar or identical to those of the tenth embodiment (FIGS. 9 to 12) are denoted at the same reference numerals in FIG. 21 and will not be described in detail.

As seen from FIG. 21, the distal portion 218 is curved at the distal end. A part of the distal end is flat. A washing nozzle 226 protrudes from the distal end of the portion 218, for applying a washing solution onto the front surface of the observation lens 225. The outlet port 226a of the nozzle 226 is positioned substantially parallel to the front surface of the observation lens 225. Since the washing nozzle 226 protrudes from the distal end of the portion 218, not from the circumferential surface thereof, with its outlet port 226a positioned substantially parallel to the distal end of the portion 218, it does not jeopardize smooth insertion of the distal portion 218 into a body cavity.

FIG. 22 is a longitudinal sectional view of the distal portion 218 of a modification of the sixteenth embodiment shown in FIG. 21. The modified endoscope is characterized in that the outlet port 226a of the washing nozzle 226 gradually narrows from the foremost part of the distal end of the portion 218 toward the peripheral edge thereof. The modified endoscope achieves the same advantage as the sixteenth embodiment (FIG. 21). The same advantages can be attained if the washing nozzle 226 is located at the flat part of the distal end of the portion 218.

Figure 24:
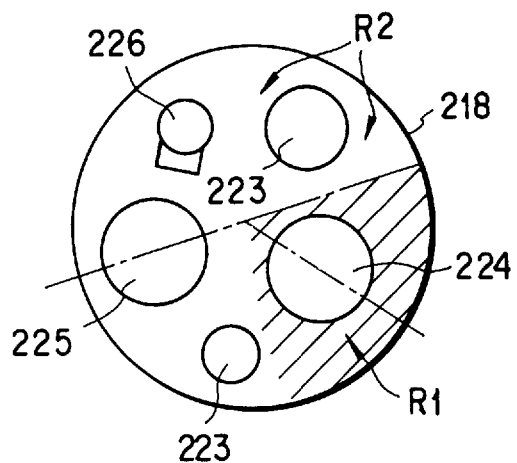
FIG. 24 is a front view of the distal portion illustrated in FIG. 23.

An endoscope according to the seventeenth embodiment of the present invention will be described, with reference to FIGS. 23 and 24. FIG. 23 is a longitudinal sectional view of the distal portion 218 of the seventeenth embodiment, and FIG. 24 is a front view of the distal portion 218. The components similar or identical to those of the tenth embodiment (FIGS. 9 to 12) are denoted at the same reference numerals in FIG. 21 and will not be described in detail.

As shown in FIG. 23, the distal portion 218 has a rounded distal end. The portion 218 incorporates an illumination lens 223 and an observation lens 225 and has a forceps channel 224. That part of the distal end at which the channel 224 opens is curved with a radius R1 of curvature. That part of the distal end at which the lenses 223, 225 are exposed is curved with a radius R2 of curvature. The radius R1 is greater than the radius R2, namely R1>R2.

The forceps can be manipulated easily however large is the radius R1 of curvature with the first-mentioned part of the distal end is curved. This is why the first-mentioned part of the distal end is curved with a relatively large radius R1 of curvature. By contrast, if the second-mentioned part of the radial end is curved with a large radius of curvature, the illumination lens 223 and observation lens 225 need to have their front surfaces inclined to their optical axes at greater angles than shown in FIG. 23. In this case, the light emitted outward through the lens 223 will decrease, and the image observed through the lens 225 will be distorted. To avoid these undesirable results, the second-mentioned part of the distal end is curved with a relatively small radius R2 of curvature. Namely, the end of the distal portion 218 is curved to ensure smooth insertion of the insertion section 214 into a body cavity, without distorted the image observed through the endoscope and without reducing the amount of light applied into the body cavity.

Since the forceps channel 224 opens at the curved distal end of the portion 218, its inner wall may contact the wall of a body cavity. The inner wall of the forceps channel 224 may be covered with an electrically insulating layer, so that an electric current would not flow to the wall of the body cavity when a medical instrument inserted in the channel 224 emits high-frequency waves.

Figure 25:
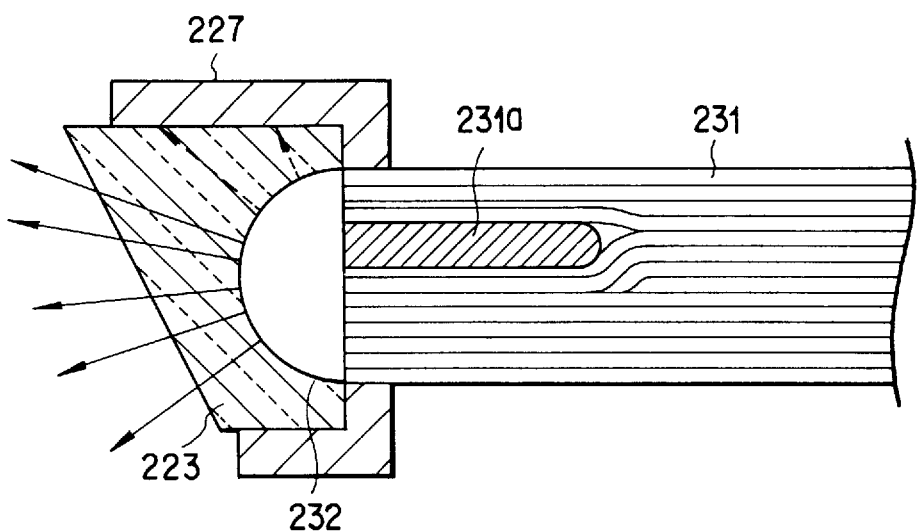
FIG. 25 is a longitudinal sectional view of the illumination optical system incorporated in an endoscope according to an eighteenth embodiment of the invention.
Figure 26:
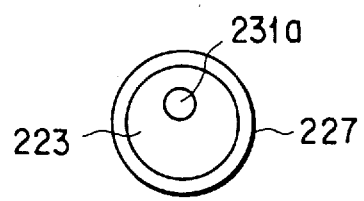
FIG. 26 is a front view of the illumination optical system illustrated in FIG. 25.

An endoscope according to the eighteenth embodiment of the invention will be described, with reference to FIGS. 25 and 26. FIG. 25 is a longitudinal sectional view of the illumination optical system built in endoscope, and FIG. 26 is a front view of the illumination optical system. The components similar or identical to those of the tenth embodiment (FIGS. 9 to 12) are denoted at the same reference numerals in FIGS. 25 and 26 and will not be described in detail.

As shown in FIG. 25, the illumination lens 223 is wedge-shaped, having its front surface inclined to its optical axis. A light guide fiber 231 is connected at its distal end to the rear of the illumination lens 223. The proximal end of the light guide 231 is connected to the light-source device (not shown). The illumination light the light-source device emits is guided through the light guide fiber 231 and applied to the rear surface 232 of the illumination lens 223. The rear surface 232 is curved so as to diffuse the illumination light.

A light guide core 231a is inserted in the distal end portion of the light guide fiber 231. As seen from FIG. 26, the core 231a is aligned with a thick part of the lens 223, not with the optical axis of the fiber 231. If the light guide core 231a were aligned with the optical axis of the lens 223, the light beam deflected at the rear surface 232 of the lens 223 and applied to a thick part of the lens 223 would be further deflected. The light beam would then reflected at the inner surface of the lens frame 227 and diffused in the illumination lens 223. Since the core 231a is aligned with the thick part of the lens 223, not with the optical axis of the fiber 231, only a small amount of light is deflected at the rear surface 232 of the lens 223, applied to the thick part of the lens 223, reflected at the inner surface of the lens frame 227 and diffused in the illumination lens 223. That is, a small part of the light applied to the lens 223 undergoes diffused reflection, and the illumination light is applied into a body cavity in uniform distribution, whereby a clear image of the interior of the body cavity can be observed through the endoscope.

Figure 27A:
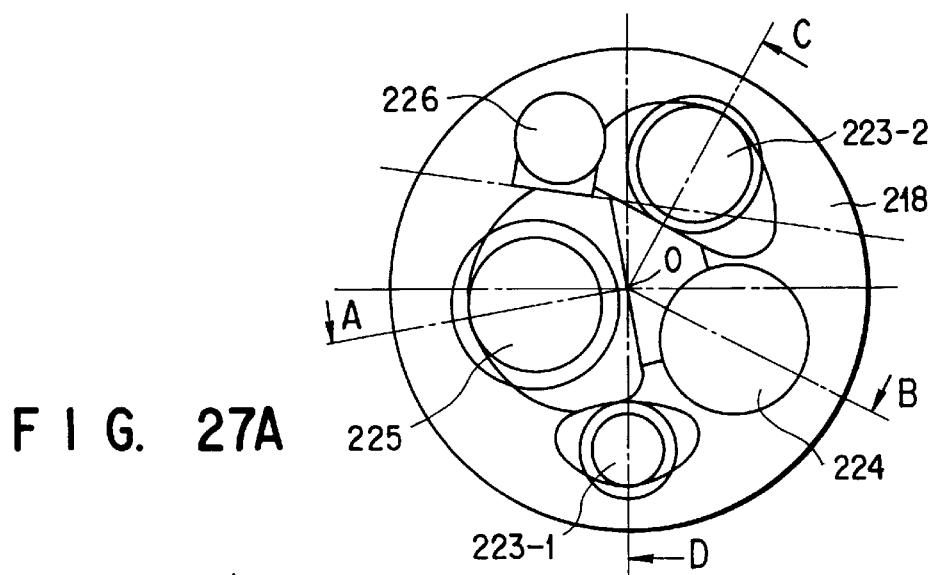
FIG. 27A is a front view of the distal portion of an endoscope according to a nineteenth embodiment of the present invention.
Figure 27B:
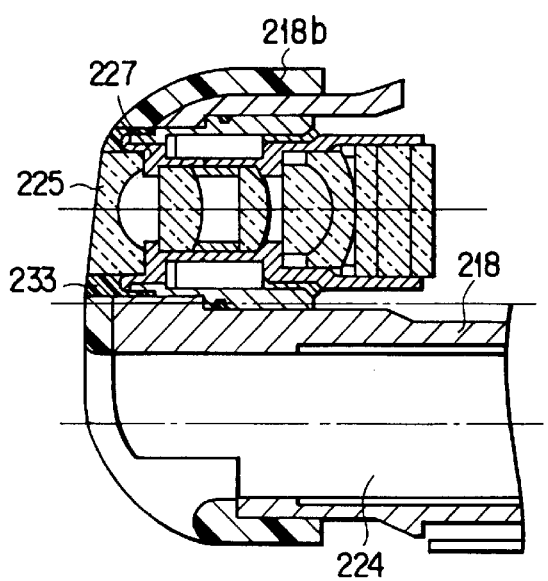
FIG. 27B is a sectional view of the distal portion, taken along line 27B-O-27B in FIG. 27A.

An endoscope according to the nineteenth embodiment of the present invention will be described, with reference to FIGS. 27A to 27C. FIG. 27A is a front view of the distal portion 218 of the nineteenth embodiment, FIG. 27B is a sectional view thereof, taken along line 27B-O-27B in FIG. 27A, and FIG. 27 C is a sectional view thereof, taken along line 27C-O-27C in FIG. 27A. The components similar or identical to those of the tenth embodiment (FIGS. 9 to 12) are denoted at the same reference numerals in FIGS. 25 and 26 and will not be described in detail.

As shown in FIG. 27B, the distal portion 218 is rounded at its distal end. Incorporated in the distal portion 218 are an illumination lens unit 223, a forceps channel 224, an observation lens unit 225 and a washing nozzle 226.

As seen from FIG. 27A, the observation lens unit 225 is positioned to the left of the axis of the distal portion 218, as viewed from the front. The forceps channel 224 is spaced from the lens unit 225 counter-clockwise at about 140°, as seen from the front. The illumination lens unit 223 has a small-diameter lens 223-1 and a large-diameter lens 223-2. The small-diameter lens 223-1 is located below the axis of the distal portion 218. The large-diameter lens 223-2 is spaced from the lens 223-1 counterclockwise by about 160°. The washing nozzle 226 is provided above the observation lens unit 225, as viewed from the front. The nozzle 226 is position such that its outlet port 226a opposes the front surface of the observation lens unit 225.

As is shown in FIG. 27B, the observation lens unit 225 comprises a plurality of lenses. The foremost lens of the unit 225 is a wedge-shaped lens. Its front surface is inclined at several degrees to the axis of the distal portion 218. The foremost lens is positioned so that its inclined front surface smoothly continues to the rounded distal end of the distal portion 218. As can be understood from FIG. 27A, a part of the distal end of the portion 218 is flat and inclined at the same angle to the axis of the portion 218 as the front surface of the foremost lens of the observation lens unit 225. It is in this flat part that the foremost lens of the unit 225 is provided. The lens of the unit 225 are held in a lens frame 227 which is shaped symmetrical to the optical axis of the observation lens unit 225. The forceps channel 224 opens at the rounded distal end of the portion 218.

Figure 27C:
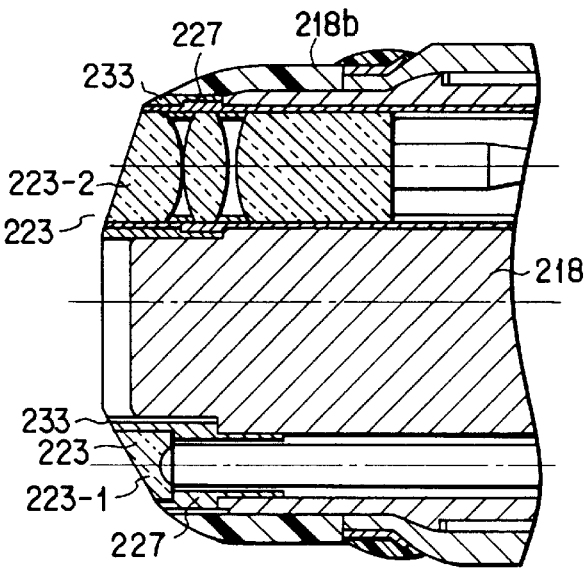
FIG. 27C is a sectional view of the distal portion, taken along line 27C-O-27C in FIG. 27A.

As illustrated in FIG. 27C, the lens 223-1 and 223-2 which have different diameters are provided in the distal end of the distal portion 218. Their front surfaces are inclined at different angles. More precisely, the front surfaces of the large-diameter lens 223-2 and the small-diameter lens 223-1 are inclined respectively at about 20° and about 30° to a plane perpendicular to the axis of the distal portion 218. Namely, the lens 223-1 which is located farther from the axis of the portion 218 than the lens 223-2 has its front surface more inclined than the front surface of the large-diameter lens 223-2. The lenses 223-1 and 223-2 are held in lens frames 227 and provided in two flat parts of the distal end of the distal portion 218, respectively. The lens frame 227 holding the small-diameter lens 223-1 has its distal end inclined at the same angle as the front surface of the lens 223-1. Similarly, the lens frame 227 holding the large-diameter lens 223-2 has its distal end inclined at the same angle as the front surface of the lens 223-2.

The lenses are fitted in the lens frames 227 and the lens frames 277 are set in the distal portion 218, such that the foremost lens in each frame 227 slightly protrudes forward from the curved distal end of the portion 218 and the distal end of each lens frame 227 recedes from the rounded distal end of the portion 218. Adhesive 233 is applied in the gap between the distal end of each lens frame 227 and the front surface of the foremost lens. The front surface of each foremost lens therefore smoothly continues to the rounded distal end of the distal portion 218.

As indicated above, the large-diameter lens 223-2 and the small-diameter lens 223-1 of the illumination lens unit 223 are wedge-shaped ones. They can be located at any desired positions in the distal portion 218, with their front surfaces inclined at such angles as to smoothly continue to the rounded distal end of the portion 218. The distal portion 218 need not be so thick as to have a rounded distal end as in the case where lenses 223-1 and 223-2 have their front surfaces not inclined at all. Further, since the stepped junction between the distal end of each lens frame 227 is filled with the adhesive 233, the distal end of the portion 218 has a smooth rounded surface, having no recesses in which filth may accumulate.

Figure 29A:
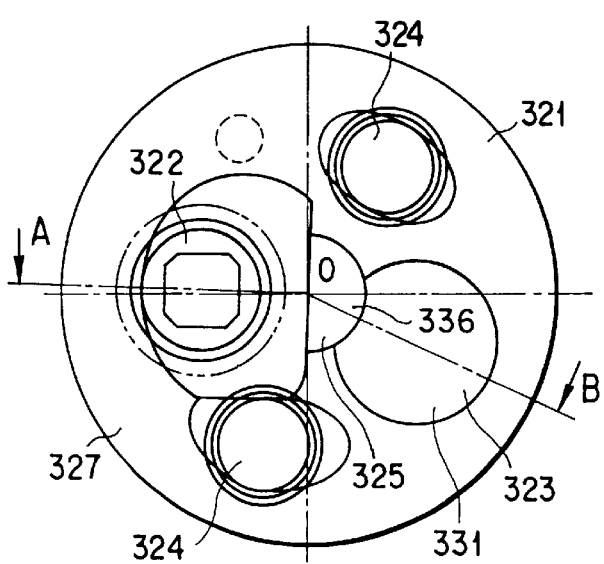
FIG. 29A is a front view of the distal portion illustrated in FIG. 28.
Figure 29B:
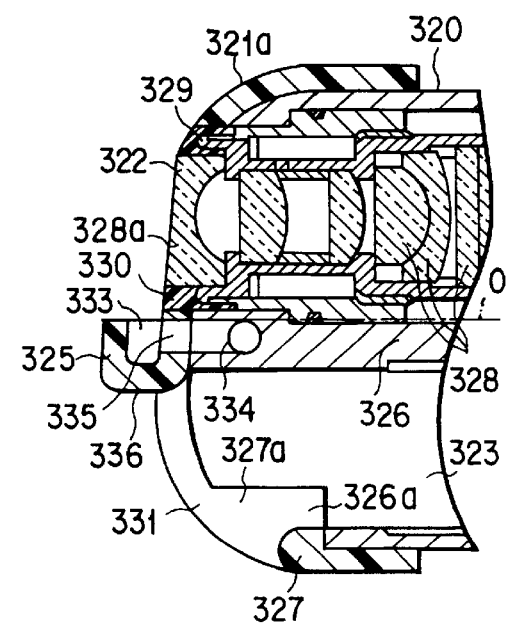
FIG. 29B is a sectional view of the distal portion, taken along line 29B-O-29B in FIG. 29A.

A video endoscope system 301 which comprises a video endoscope 302 according to the twentieth embodiment of the invention will be described with reference to FIGS. 28, 29A and 29B. FIG. 28 is a block diagram showing a video endoscope system, FIG. 29A is a front view of the distal portion illustrated in FIG. 28, and FIG. 29B is a sectional view of the distal portion, taken along line 29B-O-29B in FIG. 29A. The twentieth embodiment is a video endoscope, but the present invention can be applied to an optical-fiber endoscope, as well.

As shown in FIG. 28, the system 301 comprises the video endoscope 302, a light-source device 303, a video processor 304, a monitor 305, a VTR deck 306, a video disk drive 307, and a video printer 308. The insertion section 309 is designed to be inserted into a patient's body cavity. The operation section 310 is coupled to the proximal end of the insertion section 309.

A universal cord 311 is connected at one end to the operation section 310 and at the other end to a first connector unit 312. Connected to the connector unit 312 is one end of a signal cable 313. The other end of the cable 313 is connected to one end of a second connector unit 314. The connector units 312 and 314 are removably coupled to the light-source device 303 and the video processor 304, respectively.

The light-source device 303 contains a lamp 315, which emits light. The light is applied through a focusing lens 316 onto the light-receiving surface of the light guide 317 incorporated in the video endoscope 302. The light is guided through the light guide 317 to the distal end of the insertion section 309 and is applied outwards from the distal end.

The second connector unit 314 is removably coupled to the video processor 304. Connected to the video processor 304 are the monitor 305, VTR deck 306, video disk drive 307 and video printer 308. The video endoscope 302 incorporates a charge coupled device (CCD) and a signal line. The charge coupled device converts an optical image into an electric signal. The signal is supplied via the signal line to the video processor 304. The video processor 304 processes the signal, generating image data. The image data is supplied to the monitor 305, which display the image represented by the image data. If necessary, the image data is supplied to the VTR deck 306, the video disk drive 307 and the video printer 308.

The insertion section 309 comprises a flexible tube 318, a bending portion 319 and a distal portion 320. The flexible tube 318 is coupled at the proximal end to the operation section 310 and at the distal end to the portion 319. The distal portion 320 is coupled to the distal end of the bending portion 319. The portion 319 can be bent and straighten under remote control of the operation section 310.

As shown in FIG. 29A which is a front view of the distal portion 320, an observation lens unit 322, a forceps channel 323 and two illumination lenses 324 are provided on the distal end 321 of the portion 320, deviated from the axis O of the portion 320. A washing nozzle 325 is positioned at the center of the distal end 321, for applying a washing solution onto the front surface of the observation lens unit 322.

As seen from FIG. 29B, the distal end 321 is rounded, providing a rounded surface 321a. The distal portion 320 comprises a main body 326 and a cover 327 covering the main body 326. The washing nozzle 325 is formed integral with the cover 327.

The tip of the distal end 321 is located near the axis O of the distal portion 320. The word "tip" means the foremost part of the distal end 321, not the tip of any component other than the main body 326 of the distal portion 320, such as the washing nozzle 325.

The observation lens unit 322 comprises a plurality of lenses 328. These lenses 328 are held in a lens frame 329 which is set in the main body 326 of the distal portion 320. The lens frame 329 is symmetrical to its axis, which extends parallel to the axis O of the distal portion.

The foremost lens 328a of the observation lens unit 322 is a wedge-shaped lens. Its front surface is inclined at several degrees to the axis O of the distal portion 320. The foremost lens 328a is positioned so that its inclined front surface smoothly continues to the rounded distal end 321 of the distal portion 320. The lens 328a is asymmetrical to its axis; its thickness is not uniform.

The foremost lens 328a of the observation lens unit 322 slightly protrudes forward from the rounded distal end 321 of the portion 320. The distal end of the lens frame 329 recedes from the rounded distal end 321 of the portion 321. Adhesive 330 is applied in the gap between the distal end of the frame 329 and the front surface of the foremost lens 328a. The front surface of each foremost lens 328a therefore smoothly continues to the rounded distal end 321 of the distal portion 320. The adhesive 330 may be replaced by filler such as RTV silicone rubber.

The distal end 331 of the forceps channel 323 opens partly at the rounded surface 321a of the main body 326 and partly at the outer circumferential surface thereof. The proximal end of the forceps channel 323 communicates with an instrument insertion port 332 provided in the operation section 310.

An engagement projection 327a is formed integral with the rear end of the cover 327, extending backwards from the distal end 331 of the forceps channel 323. An engagement recess 326a is made in the distal end of the main body 326. The engagement projection 327a is removably fitted in the the engagement recess 326a. The projection 327a and the recess 326a remain fitted together with no gaps between them, as long as the cover 327 and the main body 326 are coupled with each other. The distal end 331 of the forceps channel 323 smoothly continues to the rounded front surface of the cover 327.

The washing nozzle 325 has an outlet section 333 and a connecting section 335. The outlet section 333 is bent toward the front surface of the foremost lens 328a of the observation lens unit 322. The connecting section 335 is coupled to a fluid passage 334 made in the insertion section 309. A washing solution is supplied through the fluid passage 334 into the washing nozzle 325. The solution is applied from the outlet section 333 onto the front surface of the foremost lens 328a of the observation lens unit 322. The front surface of the lens 328a is thereby washed clean.

A projection 336 protrudes from that end of the washing nozzle 325 which is opposite to the outlet section 333. As shown in FIGS. 29A and 29B, the projection 336 extends backwards, with a part located in the forceps channel 323, as long as the cover 327 remains secured to the main body 326. That is, the projection 336 protruding from the washing nozzle 325 overlaps the forceps channel 323 provided in the insertion section 309, as viewed from the front.

The video endoscope according to the twentieth embodiment is advantageous in the following respects.

First, the observation lens unit 322, the forceps channel 323, the two illumination lenses 324, the washing nozzle 325 and the other components occupy but a smaller space in the rounded surface 321a of the main body 326 than in the conventional video endoscope. This is because the projection 336, a greater part of which is positioned in front of the forceps channel 323, overlaps the forceps channel 323 as seen from the front.

Second, since all components in the distal portion 320, except the washing nozzle 325, need not be arranged in a special fashion, the forceps channel 323, the fluid passage 334, the illumination optical system, and the illumination optical system occupy only a small space in the insertion section 309. The distal portion 320 is therefore thinner than otherwise, which helps to ensure smooth insertion of the insertion section 309.

Third, since the washing nozzle 325 is aligned with the axis O of the insertion section 309, requiring no space in the distal section 320 and near the axis O, the nozzle 325 will not be caught in the inner wall of a narrow tubular organ as the distal portion 320 is guided into the organ, by maintaining the outer periphery of the distal portion 320 in contact with the inner wall of the organ. This helps to achieve smooth insertion of the insertion section 309 into the narrow tubular organ.

Fourth, a forceps can be directed away from the projection 336 of the nozzle 325 because the distal end 331 of the forceps channel 323 opens partly at the rounded surface 321a of the main body 326 and partly at the outer circumferential surface thereof. The forceps can therefore be easily guided into a body cavity even if its distal end happens to abut on the projection 336 of the washing nozzle 325.

Moreover, since the lens frame 329 is symmetrical to its axis, it need not be rotated to assume a specific position to the foremost lens 328a, with respect to the circumferential direction of the distal section 320. Therefore, the observation lens unit 322 can be assembled easily. Furthermore, since adhesive 330 is applied in the gap between the distal end of the frame 329 and the front surface of the foremost lens 328a, watertight seal is achieved between the foremost lens 328a and the lens frame 329.

Figure 30A:
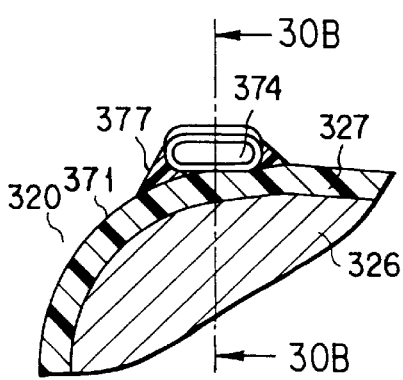
FIG. 30A is a longitudinal sectional view of a part of the distal portion of an endoscope according to a twenty-first embodiment of this invention, showing the washing nozzle provided in that part of the distal portion.
Figure 30B:
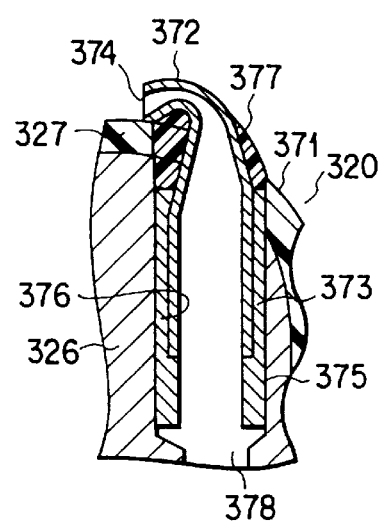
FIG. 30B is a sectional view of the distal portion, taken along line 30B—30B in FIG. 30A.

An endoscope according to the twenty-first embodiment of the invention will be described, with reference to FIGS. 30A and 30B. FIG. 30A is a sectional view of a part of the distal portion of the endoscope. FIG. 30B is a sectional view of the distal portion, taken along line 30B—30B in FIG. 30A. The twenty-first embodiment is identical to the twentieth embodiment (FIGS. 28, 29A and 29B), except that the main body 326 of the distal portion 320 has a rounded distal end 371 and that a washing nozzle 372 is mounted on the rounded distal end 371.

As shown in FIG. 30A, the washing nozzle 372 comprises a nozzle body 373 and an outlet section 374. The nozzle body 373 is a pipe extending substantially parallel to the axis of of the insertion section 309. The outlet section 374 extends outwards from the body 373 and is bent, directed to the foremost lens 328a of the observation lens unit 322. The nozzle body 373 is held in a pipe-shaped holder 375.

As shown in FIG. 30B, the cover 327 has a hole 376, which communicates with the interior of the insertion section 309. The washing nozzle 372 is fitted in the hole 376. To be more specific, the body 373 of the washing nozzle 372 is held in the pipe-shaped holder 375, which is inserted in the hole 376. The holder 375 has its distal end located inward of the outer edge of the hole 376. As seen from FIGS. 30A and 30B, adhesive 377 is applied at the stepped portion defined between the distal end of the holder 375 and the front surface of the washing nozzle 372. Hence, the front surface of the distal portion of the nozzle 372 smoothly continues to the rounded distal end 371 of the main body 326.

As mentioned above, the front surface of the distal portion of the nozzle 372 smoothly continues to the rounded distal end 371 of the main body 326, thanks to the adhesive 377 applied at said stepped portion. Therefore, the washing nozzle 372 is not likely to be caught in the inner wall of a body cavity when the insertion section 309 is inserted into the body cavity.

An endoscope according to the twenty-second embodiment of the invention will be described, with reference to FIGS. 31A and 31B. FIGS. 31A and 31B are partially sectional side views of the distal portion of the twenty-second embodiment.

The twenty-second embodiment is identical to the twentieth embodiment (FIGS. 28, 29A and 29B), except for some respects. First, the distal portion 320 has a projection 392 which is located off the center of the main body 326, as viewed from the front of the distal portion 320. Second, the observation lens unit 322 is located off the center of the main body 326, as seen from the front of the distal portion 320. Third, the observation lens unit 322 in the main body 326 is positioned such that its rectangular view field R has the upper side directed to the projection 392 of the distal portion 320 as illustrated in FIG. 31A.

If the lens unit 322 were positioned such that its rectangular view field R has one corner directed to the projection 392 as shown in FIG. 31B, a part of the projection 392 should appear in the view field R. In order to avoid this, it would be necessary to locate the lens unit 322 farther from the projection 392, inevitably increasing the outside diameter of the main body 326 of the distal portion 320.

Since the observation lens unit 322 is positioned such that its rectangular view field R has the upper side directed to the projection 392 of the distal portion 320 as shown in FIG. 31A, the projection 392 does not appear in the view field R and the lens unit 322 need not be locate at a long distance from the projection 392 to prevent a part of the projection 392 from appearing in the view field. The outside diameter of the main body 326 is therefore smaller than in the case where the lens unit 322 is positioned so as to direct one corner of its rectangular view field R to the projection 392 as shown in FIG. 31B.

An endoscope according to the twenty-third embodiment of the invention will be described, with reference to FIG. 32. FIG. 32 is a side view of the observation lens unit 322 incorporated in the endoscope.

The twenty-third embodiment is identical to the twentieth embodiment (FIGS. 28, 29A and 29B), except for the structure of the observation lens unit 322. As shown in FIG. 32, the unit 322 comprises a foremost lens 328a and four lenses 328. The lenses 328 are arranged coaxial with one another, with the common optical axis $O_2$ positioned parallel to the optical axis $O_1$ of the foremost lens 328a and shifted toward the thinner edge of the foremost lens 328a. Thus, the view field of the endoscope is directed to substantially forward.

The foremost lens 328a has a front surface $328a_1$ which is inclined to the optical axis $O_1$. The foremost lens 328a has a hemispheric concave $328a_2$ in the center part of its rear surface.

A charge coupled imaging device 411 is provided, facing the rear surface of the rearmost lens 328 of the observation lens unit 322. The foremost lens 328a is held in the distal portion 320 such that its front surface $328a_1$ smoothly continues to the rounded surface 321a of the main body 326 of the distal portion 320.

As shown in FIG. 32, the lenses 328 have a common axis $O_2$ which is parallel to the axis of the distal portion 320. Assume that a light beam is applied onto the center of the light-receiving surface of the charge coupled device 411. This beam is parallel to the axis of the distal portion 320 in front of the foremost lens 328a. As the beam passes through the foremost lens 328a, traveling from the front of the lens 328a to the back thereof, it is deflected toward the thicker edge of the lens 328. As the beam emerges from the concave back of the lens 328a, it is deflected again toward the thin edge of the lens 328a, becoming parallel to the axis of the distal portion 320. The beam finally reaches the center of the light-receiving surface of the charge coupled device 411. Since the beam, which is parallel to the axis of the portion 320 in front of the lens 328a, is applied onto the center of the light-receiving surface of the device 411, the view field of the endoscope is directed forward.

With the twenty-third embodiment it is possible to direct the view field substantially forward though the foremost lens 328a of the observation lens unit 322 is a wedge-shaped one.

Figure 33:
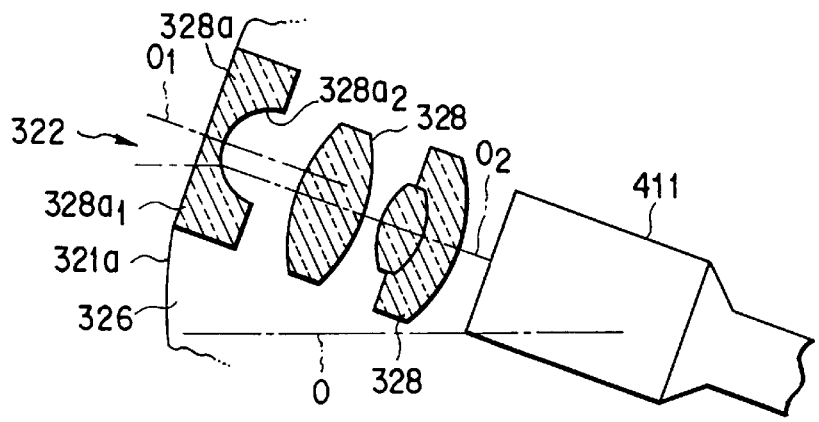
FIG. 33 is a side view of the observation lens unit incorporated in an endoscope according to a twenty-fourth embodiment of this invention.

An endoscope according to the twenty-fourth embodiment of the present invention will be described, with reference to FIG. 33. FIG. 33 is a side view of the observation lens unit 322 incorporated in the endoscope.

The twenty-fourth embodiment is identical to the twentieth embodiment (FIGS. 28, 29A and 29B), except for the structure of the observation lens unit 322. As shown in FIG. 33, the unit 322 comprises a foremost lens 328a and three lenses 328. The foremost lens 328a is symmetrical to its axis. The lenses 328 are arranged coaxial with one another, having a common optical axis $O_2$.

The foremost lens 328a has a flat front surface $328a_1$. The lens 328a is positioned with its optical axis $O_1$ inclined to the axis O of the insertion section 309. The front surface $328a_1$ is therefore inclined to a plane perpendicular to the axis O of the insertion section 309 and smoothly continues to the rounded surface 321a of the main body 326 of the distal portion 320.

The lenses 328 are arranged at the rear of the foremost lens 328a such that their common optical axis $O_2$ is parallel to the optical axis $O_1$ of the foremost lens 328a and shifted toward the axis O of the insertion section 309.

Assume that a light beam is applied onto the center of the light-receiving surface of a charge coupled device. As shown in FIG. 33, the beam is parallel to the axis O of the insertion section 309 in front of the foremost lens 328a (that is, in front of the insertion section 309). As the beam passes through the lens 328a, traveling from the front of the lens 328a to the back thereof, it is deflected toward the axis O of the section 309. As the beam emerges from the concave back of the lens 328a, it is deflected toward the axis O of the section 309, and travels along the common axis of the lens 328, reaching the center of the light-receiving surface of the charge coupled device. The view field of the endoscope is therefore directed forward as in the twenty-third embodiment.

In the twenty-fourth embodiment, nothing that may be caught in the inner wall of a body cavity is formed on the rounded surface 321a of the main body 326 of the distal portion 320. This helps to ensure smooth insertion of the insertion section 309 into the body cavity. Further, the twenty-fourth embodiment can be manufactured at low cost since the all lenses of the observation lens unit 322 are symmetrical to their respective optical axes. In addition, since its view field is directed to substantially forward, the endoscope according to the twenty-fourth embodiment can be easy to operate.

Figure 34:
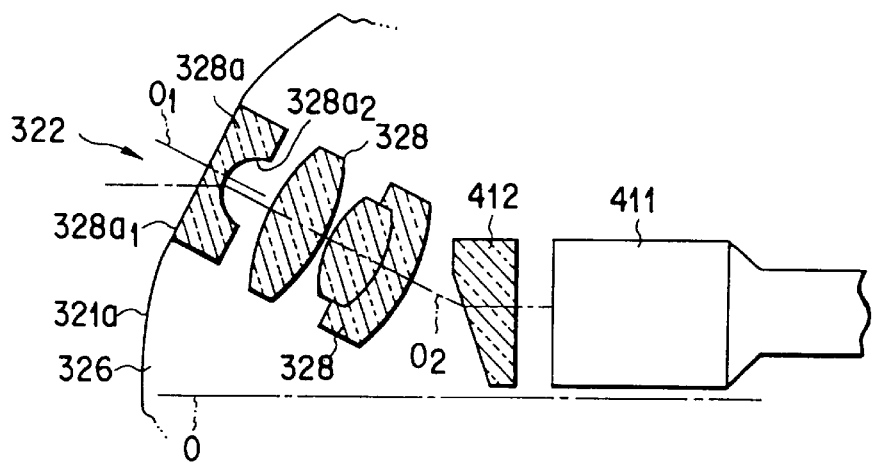
FIG. 34 is a side view of the observation lens unit incorporated in an endoscope according to a twenty-fifth embodiment of the invention.

An endoscope according to the twenty-fifth embodiment of the invention will be described, with reference to FIG. 34. FIG. 34 is a side view of the observation lens unit 322 incorporated in this endoscope.

The twenty-fifth embodiment is identical to the twenty-fourth embodiment (FIG. 33), except that a wedge-shaped prism 412 is interposed between the rearmost lens 328 and the charge coupled device 411.

The prism 412 deflects the light emitted from the rearmost lens 328 and applies the light to the charge coupled device 411, along a line substantially parallel to the axis O of the insertion section 309. Hence, the arrangement of the lenses 328a and 328 can be adjusted in the main body 326 of the distal portion 320. The freedom of design of the observation lens unit 322 is therefore high.

Figure 35A:
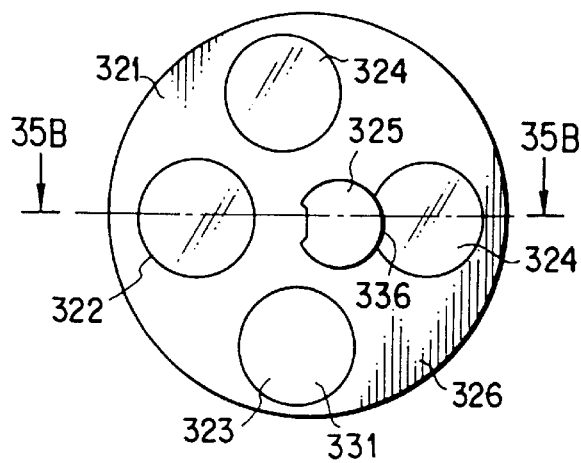
FIG. 35A is a front view of the distal portion of an endoscope according to a twenty-sixth embodiment of the present invention.
Figure 35B:
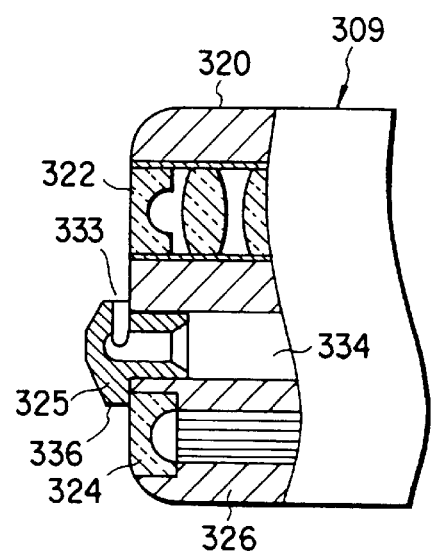
FIG. 35B is a sectional view of the distal portion, taken along line 35B—35B in FIG. 35A.

An endoscope according to the twenty-sixth embodiment of the present invention will be described, with reference to FIGS. 35A and 35B. The twenty-sixth embodiment is identical to the twentieth embodiment (FIGS. 28, 29A and 29B), except for only one aspect. That is, the projection 336 of the washing nozzle 325 is bent so that its outer end is located before the distal end of the distal portion 320 as shown in FIG. 35A and overlaps a part of the lens 324 as viewed from the front as illustrated in FIG. 35B.

Since the projection 336 of the washing nozzle 325 overlaps a part of the lens 324 as viewed from the front of the distal portion 320, the observation lens unit 322, the forceps channel 323, the two illumination lenses 324, the washing nozzle 325 and the other components occupy but a smaller space than otherwise in the rounded surface 321a of the main body 326. Therefore, the distal portion 320 can be thinner than in the conventional endoscope, to help ensure smooth insertion of the insertion section 309.

An endoscope according to the twenty-seventh embodiment of the invention will be described with reference to FIGS. 36 and 37. FIG. 36 is a front view of the distal portion of this endoscope, and FIG. 37 is a sectional view of the distal portion, taken along line 37-O-37 in FIG. 36.

As seen from FIG. 37, the distal portion 401 has a rounded distal end 421. Provided in the distal end 421 are two illumination lenses 422 and 423, a forceps channel 424, an observation lens unit 425 and a washing nozzle 426. The nozzle 426 is designed to wash the front surface $425a_1$ of the foremost lens 425a.

The upper part of the distal portion 401 is located at the upper side of the rectangular view field of the endoscope. The distal portion 401 is a cylinder. Hereinafter, the axis O of the distal portion 401 will be referred to as "the axis of the endoscope." The observation lens unit 425 is located below the axis O of the endoscope.

As can be understood from FIG. 37, the observation lens unit 425 comprises a plurality of lenses including the foremost lens 425a. The foremost lens 425a is a wedge-shaped one. It has a flat front surface $425a_1$ which is inclined, not perpendicular, to the optical axis $O_{11}$ of the lens unit 425. Inclined to the optical axis $O_{11}$, the front surface $425a_1$ of the foremost lens 425a smoothly continues to the surface of the rounded distal end 421 of the distal portion 401. The other lenses of the observation lens unit 425 have a common optical axis which is parallel to the axis O of the endoscope.

The distal portion 401 is connected to the bending portion 19 (FIG. 1) which can be bent by operating the operation section (not shown) of the endoscope.

As mentioned above, the foremost lens 425a of the observation lens unit 425 is a wedge-shaped lens in the twenty-seventh embodiment.

Assume that a light beam is applied onto the center of the light-receiving surface of a charge coupled device. The upper part of the distal portion 401, as viewed in FIG. 37, corresponds to the upper side of the view field of the endoscope. In front of the distal portion 401, the beam inclines to the upper side of the view field and is not parallel to the axis of the portion 401. As the beam passes through the foremost 425a, traveling from the front of the lens 425a to the back thereof, it is deflected, becoming parallel to the axis of the distal portion 401. Then, the beam emerges from the center of the concave back of the lens $425a_1$. It then travels along the common axis of the lens 425, reaching the center of the light-receiving surface of the charge coupled device. Since the beam, which inclines to the upper side of the view field in front of the distal portion 401, is applied onto the center of the light-receiving surface of the device 411, the view field of the endoscope is directed toward the upper part of the distal portion 401.

Since the upper half of the foremost lens 425a is thicker than the lower half which is nearer to the outer circumferential surface of the distal portion 401, the view-field direction inclines toward the axis O of the endoscope. That is, since the observation lens unit 425 is located below the axis O of the endoscope, the view-field direction inclines upwards.

Since the view-field direction inclines upwards, the duodenum and a corner of the stomach are seen in the view field of the endoscope when the distal portion 401 of an endoscope is guided to the lower end of the stomach. Were the view-field direction parallel to the optical axis $O_{11}$, the duodenum or a corner of the stomach would be located outside the view field of the endoscope and could hardly be observed through the endoscope.

An endoscope according to the twenty-eighth embodiment of this invention will be described, with reference to FIGS. 38 and 39. As can be seen from FIGS. 38 and 39, the twenty-eighth embodiment is identical to the twenty-seventh embodiment (FIGS. 36 and 37), except for three respects. First, the observation lens unit 425 is located above the axis O of the insertion section as shown in FIG. 38. Second, the foremost lens 425a of the unit 425 is symmetrical to its axis. Third, the optical axis $O_{12}$ of the unit 425 is inclined upwards, not parallel to the axis O of the insertion section, as is illustrated in FIG. 39.

Since the view-field direction inclines upwards, the twenty-eighth embodiment shown in FIGS. 38 and 39 can achieve the same advantage as the twenty-seventh embodiment (FIGS. 36 and 37).

Figure 40:
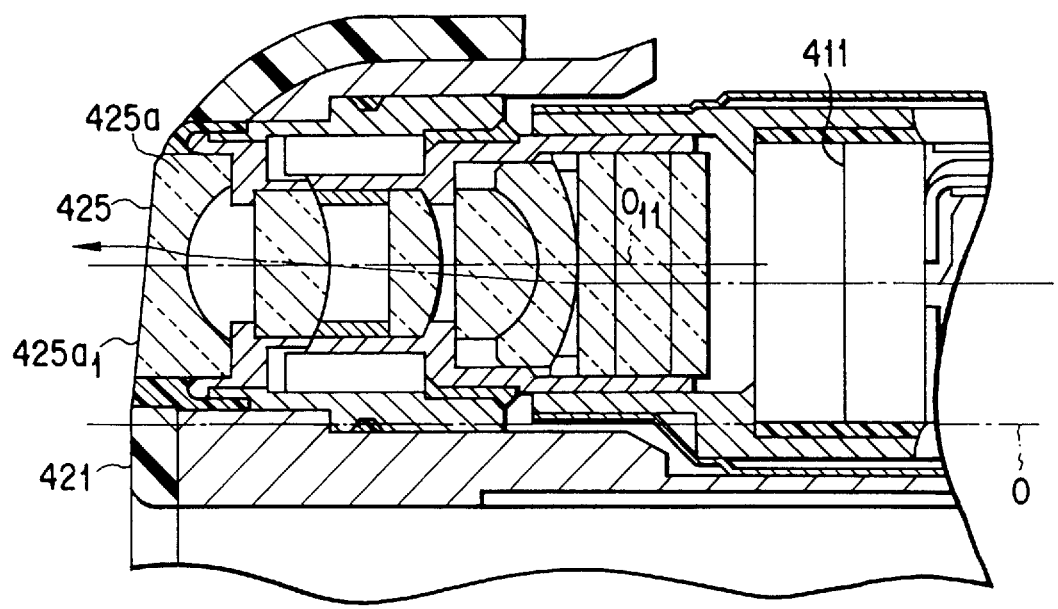
FIG. 40 is a longitudinal sectional view of the distal portion of an endoscope according to a twenty-ninth embodiment of the invention.

An endoscope according to the twenty-ninth embodiment of the present invention will be described with reference to FIG. 40. FIG. 40 is a longitudinal sectional view of the distal portion of the twenty-ninth embodiment of the invention.

As shown in FIG. 40, an observation lens unit 425 is provided in the distal portion. A charge coupled device 411 is provided at the rear end of the observation lens unit 425. The lens unit 425 comprises a plurality of lenses. These lenses focus the light input to the unit 425, on the light-receiving surface of the charge coupled device 411. The device 411 generates an image signal from the light it has received.

The foremost lens 425a of the observation lens unit 425 is a wedge-shaped lens having a flat front surface $425a_1$ which is not perpendicular to the optical axis $O_{11}$ of the observation lens unit 425. Inclined to the optical axis $O_{11}$, the front surface $425a_1$ of the foremost lens 425a smoothly continues to the surface of the rounded distal end 421 of the distal portion. The center of the charge coupled device 411 is not aligned with the optical axis $O_{11}$ of the observation lens unit 425.

A light beam applied to the observation lens unit 425, along a line parallel to the optical axis $O_{11}$ of the unit 425, is deflected by the foremost lens 425a of the unit 425 whose front surface $425a_1$ is inclined to the optical axis $O_{11}$.

A light beam applied to the unit 425, along a line parallel to the optical axis $O_{11}$ of the unit 425, reaches the center of the device 411 after deflected by the foremost lens 425a. This is because the center of the charge coupled device 411 is not aligned with the optical axis $O_{11}$ of the observation lens unit 425. Thus, the view-field direction is parallel to the axis O of the insertion section. Since the view-field direction is parallel to the axis O of the distal portion, the endoscope can be easily operated despite that the distal portion is rounded at its distal end 421 to be smoothly inserted into a body cavity.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope having an insertion section to be inserted into a tubular cavity and an observation lens provided in a distal end of the insertion section and defining a view field at an angle to an insertion direction of the insertion section, said endoscope further comprising:

a rounded distal portion protruding from the distal end of said insertion section in the insertion direction, said rounded distal portion having a forwardmost tip; and wherein said observation lens is located in the area of said tip and faces a portion of said rounded digital portion, and is located such that a center axis of said observation lens is not on a center axis of said insertion section and a center of said observation lens is displaced from said tip of said rounded distal portion.

2. The endoscope according to claim 1, wherein said observation lens is located in the tip and has a front surface smoothly continuing to a curved surface of said rounded distal portion.

3. The endoscope according to claim 1, wherein said rounded distal portion has a distal end which is entirely rounded.

4. The endoscope according to claim 1, wherein said insertion section incorporates components including an illumination optical system, an observation optical system, a forceps channel, and an air/water supplying tube.

5. The endoscope according to claim 1, wherein the tip of said rounded distal portion is located on the center axis of said insertion section.

6. The endoscope according to claim 1, wherein the tip of said rounded distal portion is located off the center axis of said insertion section.

7. The endoscope according to claim 1, further comprising a washing nozzle provided on the distal end of said distal portion and having an outlet port located at the tip of said rounded distal portion, for washing said observation lens.

8. The endoscope according to claim 7, wherein said washing nozzle is aligned with the axis of said insertion section.

9. The endoscope according to claim 4, further comprising a washing nozzle provided at the distal end of said distal portion and overlapping at least one of said components.

10. The endoscope according to claim 1, further comprising a washing nozzle provided on the distal end of said distal portion and having a connecting part smoothly continuing to the rounded a curved surface of said rounded distal portion.

11. The endoscope according to claim 1, which further comprises imaging means located at a focal point of said observation lens, for converting an image supplied through said observation lens into an electric signal, and a monitor for displaying an image represented by the electric signal generated by said imaging means, and in which said observation lens is substantially rectangular, providing a view field similar in shape to a light-receiving surface of said imaging means or a display screen of said monitor, and has one side directed to the tip of said rounded distal portion.

12. The endoscope according to claim 1, wherein said observation lens has a lens unit comprised of a plurality of lens juxtaposed along an optical axis, the foremost of the lenses is a wedge-shaped lenses formed asymmetric to an axis, has a thickness gradually changing from one edge to another and has a front surface smoothly continues to a curved surface of said rounded distal portion.

13. The endoscope according to claim 12, wherein the foremost lens has an axis which is displaced from a common axis of the other lenses, thereby causing a view-field direction of the foremost lens to extend substantially forward.

14. The endoscope according to claim 1, wherein said observation lens has a lens unit comprised of a plurality of lenses juxtaposed along an optical axis, and has an optical axis inclined to an axis of said insertion section.

15. The endoscope according to claim 14, wherein the foremost lens has an axis which is displaced from a common axis of the other lenses, thereby causing a view-field direction of the foremost lens to extend substantially forward despite that the optical axis of said lens unit is inclined to the axis of said insertion section.

16. The endoscope according to claim 1, wherein a curved surface of said rounded distal portion has a flat part at which an optical lens is to be provided.

17. The endoscope according to claim 1, wherein said insertion section includes a bundle of optical fibers, an illumination lens is provided in the distal end of the insertion section and opposes an output end of said bundle of optical fibers, said illumination lens comprises a wedge-shaped lens having a thickness gradually changing from one edge to another, and said bundle of optical fibers has a rod-shaped core displaced from an axis of the bundle toward the thicker edge of said illumination lens.

18. The endoscope according to claim 1, wherein said observation lens comprises a wedge-shaped lens formed asymmetric to an axis and having a thickness gradually changing from one edge to another, is held in a lens frame formed symmetric to an axis, and an adhesive is applied at a stepped junction between said observation lens and said lens frame, rendering smooth the distal end of said insertion section.

19. The endoscope according to claim 1, wherein said insertion section comprises a forceps channel for guiding a medical instrument, and the distal end of said insertion section has a part at which said forceps channel opens and which is curved with a larger radius of curvature than any other part.

20. The endoscope according to claim 1, wherein said observation lens is positioned, having a view-field direction inclined upward to an axis of said insertion section.

21. The endoscope according to claim 1, further comprising:
   imaging means located at a focal point of said observation lens, for converting an image supplied through said observation lens into an electric signal; and
   a monitor for displaying an image represented by the electric signal generated by said imaging means; and
   wherein the axis of said imaging means is displaced from an axis of said observation lens, thereby causing a view-field direction of said observation lens to extend substantially parallel to an axis of said insertion section.

22. The endoscope according to claim 1, further comprising a washing nozzle provided on the distal end of said distal portion and having an outlet port located above the tip of said rounded distal portion and near an upper side of a view field of said observation lens.

23. An endoscope having an insertion section to be inserted into a tubular cavity and an observation lens provided in a distal end of the insertion section and defining a view field substantially equal to an insertion direction of the insertion section, said endoscope further comprising:

a rounded distal portion protruding from the distal end of said insertion section in the insertion direction, said rounded distal portion covering said distal end of the insertion section and having a forwardmost tip; and wherein said observation lens is located in the area of said tip and faces a portion of said rounded distal portion, and is located such that a center axis of said observation lens is not on a center axis of said insertion section and a center of said observation lens is displaced from said tip of said rounded distal portion.

* * * * *

UNITED STATES PATENT AND TRADEMARK OFFICE
CERTIFICATE OF CORRECTION

PATENT NO. : 5,871,440                           Page 1 of 2
DATED      : February 16, 1999
INVENTOR(S): Yuta OKADA It is certified that error appears in the above-identified patent and that said Letters Patent is hereby corrected as shown below:

<u>On the Title page</u>, Item [57] ABSTRACT, line 8, change "forewardmost" to --forwardmost--.

Item [56] References Cited, under "U.S. PATENT DOCUMENT", line 1, change "Koyasu" to --Koyasu et al.--.

<u>Column 27</u>, line 54, change "digital" to --distal--.

In the DRAWINGS,

Figs. 41A, 41B, 41C, and 41D should each be labelled --Prior Art--,

Fig. 27A, change "A" to --27B--, change "B" to --27B--,

UNITED STATES PATENT AND TRADEMARK OFFICE
CERTIFICATE OF CORRECTION

PATENT NO. : 5,871,440
DATED : February 16, 1999
INVENTOR(S) : Yuta OKADA

It is certified that error appears in the above-identified patent and that said Letters Patent is hereby corrected as shown below:

```
                  change "C" to --27C--,
                  change "D" to --27C--,
    Fig. 29A,     change "A" to --29B--,
                  change "B" to --29B--,
    Fig. 36,      change "A" to --37--,
                  change "B" to --37--,
    Fig. 38,      change "A" to --39--,
                  change "B" to --39--.
```

Signed and Sealed this

Thirtieth Day of November, 1999

Attest:

Q. TODD DICKINSON

Attesting Officer

Acting Commissioner of Patents and Trademarks